US012780791B2

(12) United States Patent
Royo Bargués et al.

(10) Patent No.: US 12,780,791 B2
(45) Date of Patent: Nov. 3, 2026

(54) ANTITUMORAL ASCORBIC ACID ESTERS

(71) Applicant: SUIGENERIS FARMACOSMETICS, S.L., Barcelona (ES)

(72) Inventors: Teresa Royo Bargués, Barcelona (ES); Yagamare Fall Diop, Vigo (ES); María Generosa De Los Angeles Gómez Pacios, Vigo (ES); Hugo Santalla Garcia, Vigo (ES); Fatima Garrido Fernandez, Vigo (ES); Guido Kurz, Esplugues de Llobregat (ES); María Rúbies Royo, Barcelona (ES)

(73) Assignee: SUIGENERIS FARMACOSMETICS, S.L., Barcelona (ES)

( * ) Notice: Subject to any disclaimer, the term of this patent is extended or adjusted under 35 U.S.C. 154(b) by 822 days.

(21) Appl. No.: 18/043,620

(22) PCT Filed: Sep. 13, 2021

(86) PCT No.: PCT/EP2021/075104
§ 371 (c)(1),
(2) Date: Mar. 1, 2023

(87) PCT Pub. No.: WO2022/053679
PCT Pub. Date: Mar. 17, 2022

(65) Prior Publication Data

US 2023/0278974 A1 Sep. 7, 2023

(30) Foreign Application Priority Data

Sep. 14, 2020 (EP) .................................... 20382804

(51) Int. Cl.
*C07D 307/33* (2006.01)
*A61P 35/04* (2006.01)

(52) U.S. Cl.
CPC ............ *C07D 307/33* (2013.01); *A61P 35/04* (2018.01)

(58) Field of Classification Search
CPC ........ A61P 35/00; A61P 35/04; C07D 307/32; C07D 307/33; A61K 31/365
See application file for complete search history.

(56) References Cited

U.S. PATENT DOCUMENTS

| | | | | |
|---|---|---|---|---|
| 2012/0115897 A1* | 5/2012 | Tang | ........................ | C12P 17/04 435/126 |
| 2021/0283100 A1 | 9/2021 | Miller et al. | | |

FOREIGN PATENT DOCUMENTS

| | | |
|---|---|---|
| CN | 106139151 A | 11/2016 |
| WO | 2018/026673 A1 | 2/2018 |

OTHER PUBLICATIONS

Lovly et al., Tumor Heterogeneity and Therapeutic Resistance, 2016 Asco Educational Book, e585-e593, 2016 (Year: 2016).*
T. W. Greene and P. G. M. Wuts, "Protection for the Hydroxyl Group, Including 1,2- and 1,3-Diols", Protective Groups in Organic Synthesis, Third Edition, 1999, Chapter 2, pp. 17-245, John Wiley & Sons, Inc.
M. Vizoso, et al., "Epigenetic activation of a cryptic TBC1D16 transcript enhances melanoma progression by targeting EGFR", Nat Med., Jul. 2015, pp. 741-750, vol. 21(7).
Nina Mikirova, et al., "Continuous intravenous vitamin C in the cancer treatment: reevaluation of a Phase I clinical study", Functional Foods in Health and Disease, Mar. 29, 2019, pp. 180-204, vol. 9, No. 3.
The International Search Report and Written Opinion issued in corresponding International PCT Application No. PCT/EP2021/075104; Mailing Date: Nov. 11, 2021.

* cited by examiner

*Primary Examiner* — Kortney L. Klinkel
*Assistant Examiner* — Padmaja S Rao
(74) *Attorney, Agent, or Firm* — Chrisman Gallo Tochtrop LLC

(57) ABSTRACT

A compound of formula (I), or a pharmaceutically acceptable salt thereof, or a stereoisomer thereof or mixture of stereoisomers, wherein n is an integer from 0 to 10; $R_1$ is a biradical selected from the group consisting of $CH_2$, O, NH and S; and $R_2$ is a $(C_3\text{-}C_{15})$alkyl radical. Pharmaceutical compositions comprising the compound of formula (I). Methods of treating or preventing a neoplastic disease, such as pancreatic cancer.

12 Claims, 7 Drawing Sheets

ANTITUMORAL ASCORBIC ACID ESTERS

CROSS-REFERENCE TO RELATED APPLICATIONS

This is a National Stage application of PCT international application PCT/EP2021/075104, filed Sep. 13, 2021, which claims priority to European Patent Application EP20382804, filed on Sep. 14, 2020, both of which are incorporated herein by reference.

TECHNICAL FIELD

The present invention relates to the field of antineoplastic compounds, in particular to antitumoral ascorbic acid esters and antitumoral compositions comprising said esters.

The invention also relates to the use of said esters and said compositions for the prophylactic or therapeutic treatment of cancer.

BACKGROUND ART

Cancer is a group of diseases involving abnormal cell growth with the potential to invade or spread to other parts of the body. Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Each of these therapies has varying degrees of efficacy and is accompanied with multiple side effects. These side effects, together with the multidrug resistance already disclosed for traditional chemotherapy, have prompted urgent needs for novel anticancer drugs or therapeutic approaches.

One particularly deadly type of cancer is pancreatic cancer. This type of cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

Current treatment procedures available for pancreatic cancer have not led to a cure, nor to a substantially improved survival time. Surgical resection has been the only modality that offers a chance at survival. However, due to a large tumor load, only 10% to 25% of patients are candidates for “curative resection”. For those patients undergoing a surgical treatment, the five-year survival rate is still poor, averaging only about 10%. Therefore, pancreatic cancer is one of the types of cancer where there is a higher need of development of efficient therapies.

One molecule which has been long recognized as a potential anticancer agent is ascorbic acid—also known as vitamin C. However, ascorbic acid presents a very limited bioavailability and it has been shown to induce in some conditions acute oxalate nephropathy.

To overcome the limitations to the use of ascorbic acid as an anticancer molecule, a number of novel ascorbic acid derivatives have been developed in the last years by modifying its hydroxyl groups. Among them, fatty acid esters of ascorbic acid, ascorbyl palmitate and ascorbyl stearate, have attracted considerable interest as anticancer compounds due to their lipophilic nature and easy passage across cell membranes and the blood-brain barrier.

However, ascorbyl fatty acid esters present several drawbacks as a result of their high hydrophobicity. In particular, they are very difficult to handle and dissolve to obtain homogenous liquid compositions that can be easily administered into the patients.

Therefore, in spite of the efforts made so far, there is still a need for compounds with high antitumoral activities that are easy to handle and to administrate into patients.

SUMMARY OF INVENTION

The present inventors have developed various ascorbic acid esters capable of inhibiting the growth of cancer cells.

Surprisingly, the inventors have found that the esterification of ascorbic acid with a group comprising a cycloalkyl attached to an alkyl carbon chain results in compounds with a moderate degree of hydrophobicity that present a potent cancer inhibitory activity.

As shown in the examples below, the compounds herein provided are effective to inhibit the growth of cancer cells from various origins, such as pancreatic cancer cells, melanoma cells, colon cancer cells, or gastric cancer cells. Notably, the compounds of the invention are also effective when applied to metastatic cell lines, which is indicative of their capability to treat cancers in advanced stages.

The compounds of the invention are highly specific, being capable of specifically target cancer cells. That is, the compounds are able to discriminate between normal and cancer cells. This means a great advance in the field of cancer treatment as most side-effects of current anti-cancer therapies are due to the lack of specificity of anti-tumoral compounds. This specificity towards cancer cells also explains the experimental data provided below, supporting the non-toxicity of said compounds when they are administered to human primary cells (see FIG. 13).

These properties make the compounds of formula (I) of the invention suitable for the treatment of cancer.

Importantly, the compounds herein provided, in spite of comprising alkyl carbon chains, display a moderate hydrophobicity that facilitates their solubility and stability in solution, which greatly facilitates their formulation and use in the clinic.

The combination of physicochemical properties and biological activity of the compounds of the invention make them an important pharmacological alternative in the treatment of yet practically incurable tumors, like pancreatic tumors.

Thus, in a first aspect, the invention provides a compound of formula (I), or a pharmaceutically acceptable salt thereof, or a stereoisomer thereof or mixture of stereoisomers:

(I)

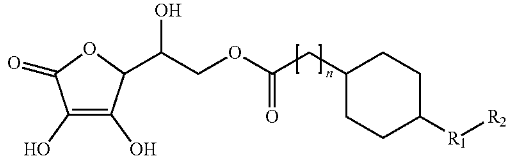

wherein n is an integer from 0 to 10; $R_1$ is a biradical selected from the group consisting of $CH_2$, O, NH and S; and $R_2$ is a $(C_3-C_{15})$alkyl radical.

In a second aspect, the invention provides a pharmaceutical composition comprising a therapeutically effective amount of the compound as defined in the first aspect with at least one pharmaceutically acceptable excipient, diluent or carrier.

In a third aspect, the invention provides the compound as defined in the first aspect or the pharmaceutical composition as defined in the second aspect, for use as a medicament.

In a fourth aspect, the invention provides the compound as defined in the first aspect or the pharmaceutical composition as defined in the second aspect, for use in the treatment or prevention of a neoplastic disease.

In a fifth aspect, the invention provides a preparation process of a compound of formula (I) as defined in the first aspect, comprising a) submitting a compound of formula (II) to a esterification reaction with a compound of formula (III), and b) deprotecting the resulting compound from (a), wherein n is an integer from 0 to 10; $R_1$ is a biradical selected from the group consisting of $CH_2$, O, NH and S; $R_2$ is a $(C_3$-$C_{15})$alkyl radical; and PG is a hydroxyl protective group.

(II)

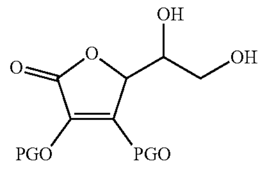

(III)

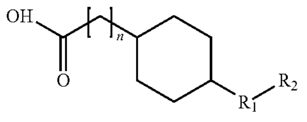

DETAILED DESCRIPTION OF THE INVENTION

Figure 1:
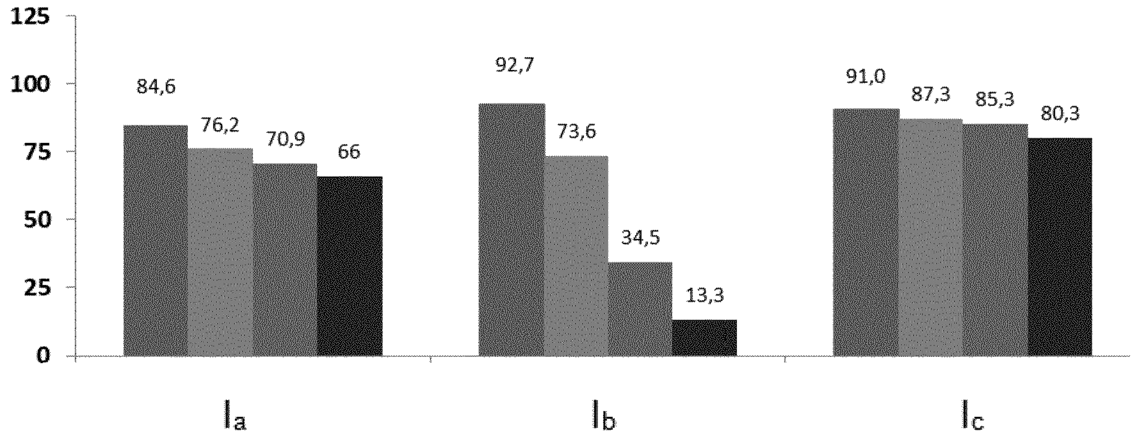
FIG. 1, is a bar diagram showing the inhibitory effect of various compounds of the invention at four different concentrations (first column form the left: 0.1 mM; second column form the left: 0.2 mM; third column form the left: 0.25 mM; and fourth column form the left: 0.3 mM) on the growth of IGR39 human primary melanoma cells in comparison to mock treated cells. The y-axis represents the number of cells after 72 h of treatment as a percentage of the number of mock treated cells, which is accorded a 100% value. The structure of compounds $I_a$, $I_b$ and $I_c$ is provided below.
Figure 2:
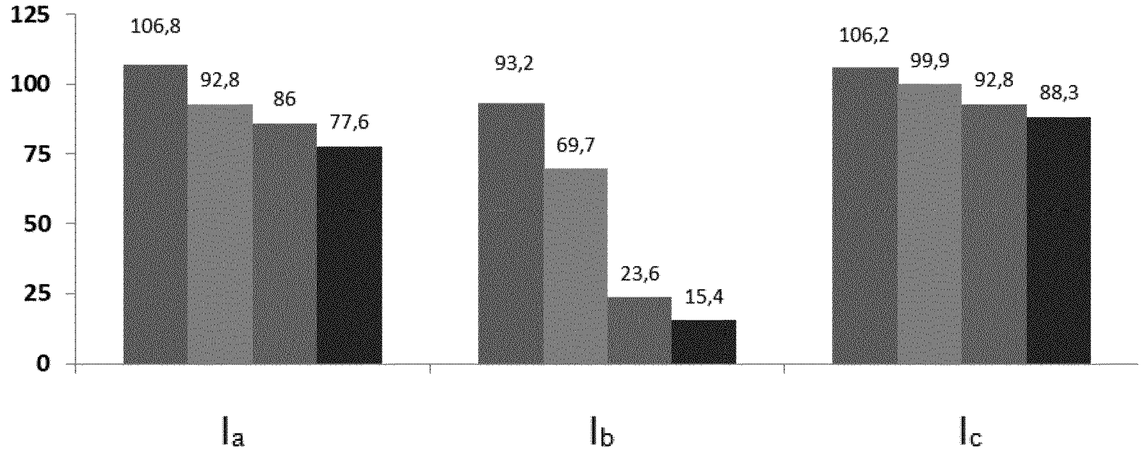
FIG. 2, is a bar diagram showing the inhibitory effect of various compounds of the invention on the growth of IGR37 human metastatic melanoma cells in comparison to mock treated cells. The above description of FIG. 1 regarding the columns, compounds, and y-axis equally apply to this Figure.
Figure 3:
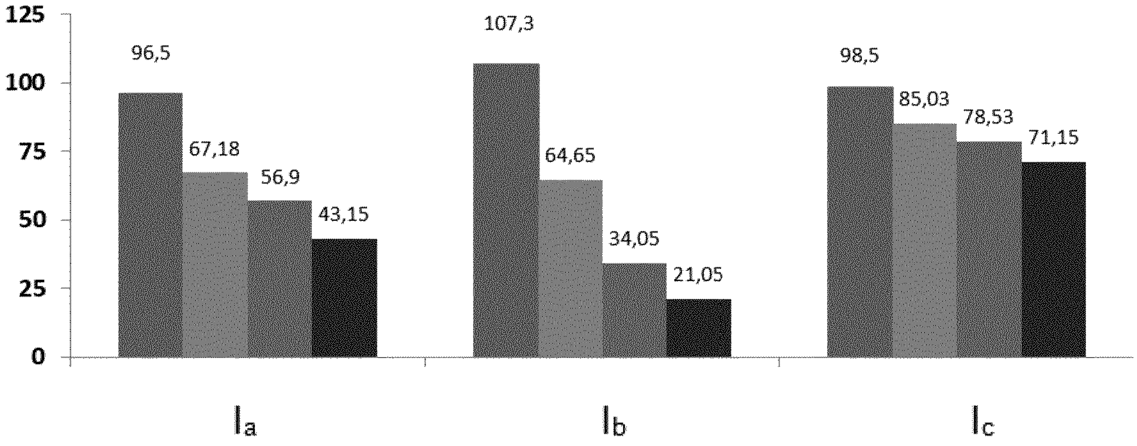
FIG. 3, is a bar diagram showing the inhibitory effect of various compounds of the invention on the growth of MW115 human primary melanoma cells in comparison to mock treated cells. The above description of FIG. 1 regarding the columns, compounds, and y-axis equally apply to this Figure.
Figure 4:
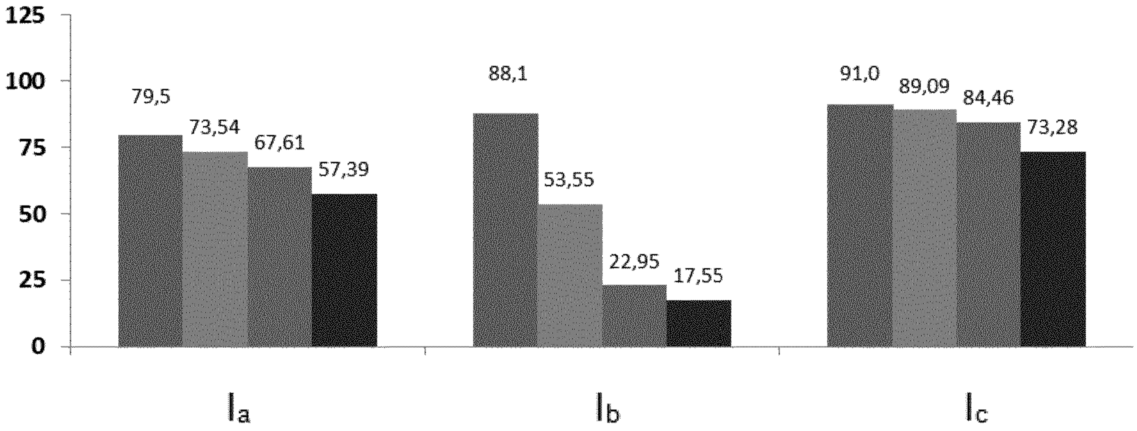
FIG. 4, is a bar diagram showing the inhibitory effect of various compounds of the invention on the growth of MW266.4 human metastatic melanoma cells in comparison to mock treated cells. The above description of FIG. 1 the columns, compounds, and y-axis equally apply to this Figure.
Figure 5:
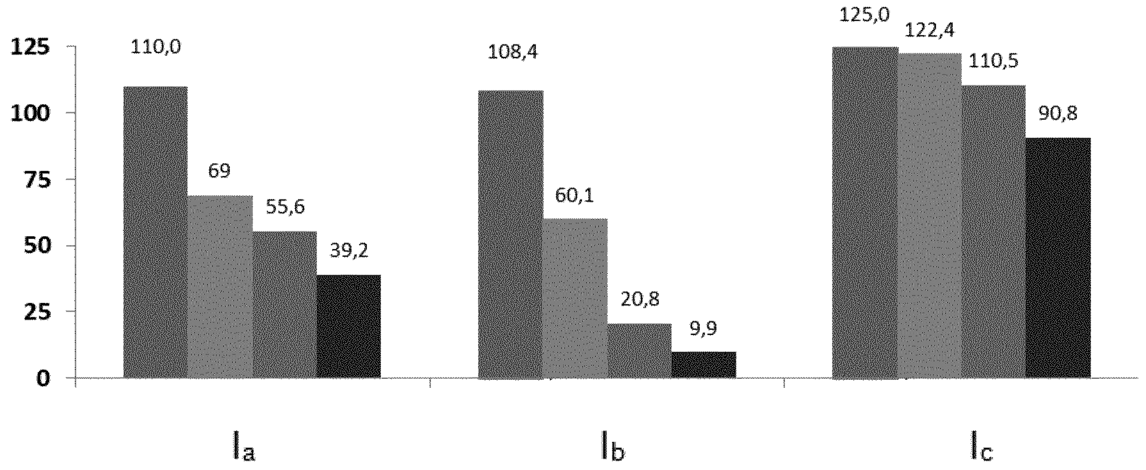
FIG. 5, is a bar diagram showing the inhibitory effect of various compounds of the invention on the growth of DLD1 human colon cancer cells in comparison to mock treated cells. The above description of FIG. 1 regarding the columns, compounds, and y-axis equally apply to this Figure.
Figure 6:
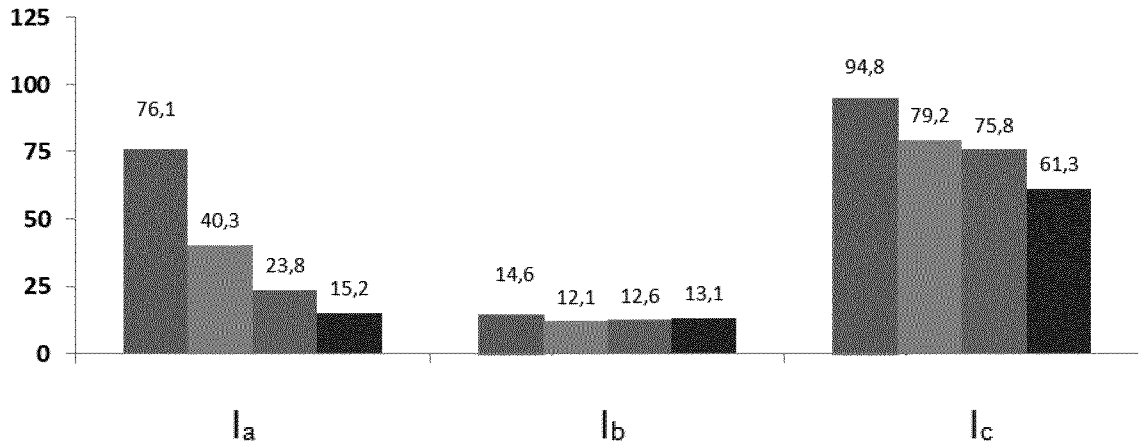
FIG. 6, is a bar diagram showing the inhibitory effect of various compounds of the invention on the growth of SW480 human colon cancer cells in comparison to mock treated cells. The above description of FIG. 1 regarding the columns, compounds, and y-axis equally apply to this Figure.
Figure 7:
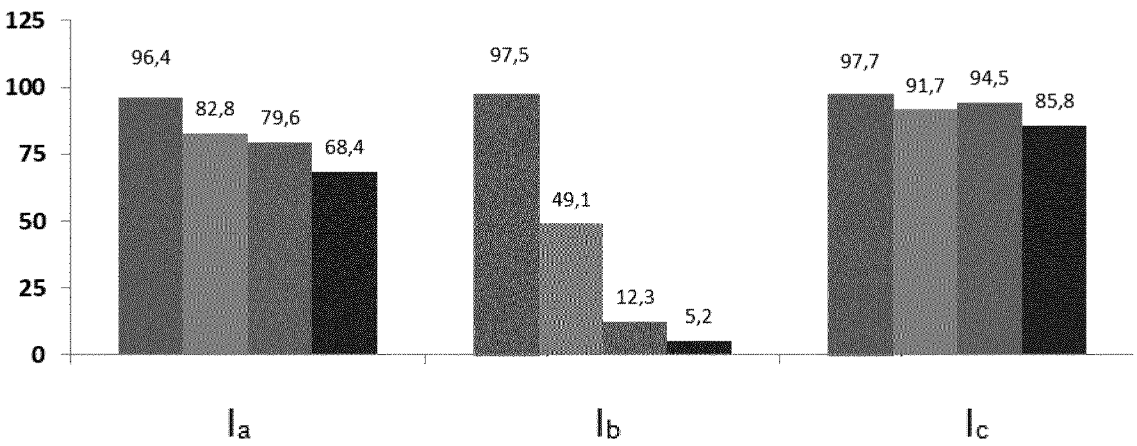
FIG. 7, is a bar diagram showing the inhibitory effect of various compounds of the invention on the growth of HCT116 human colon cancer cells in comparison to mock treated cells. The above description of FIG. 1 regarding the columns, compounds, and y-axis equally apply to this Figure.
Figure 8:
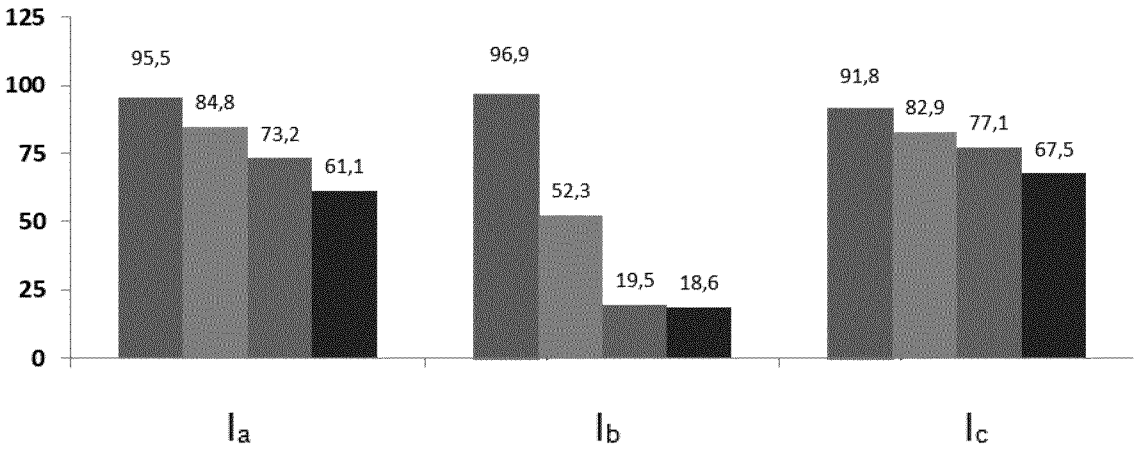
FIG. 8, is a bar diagram showing the inhibitory effect of various compounds of the invention on the growth of NUG-C4 human gastric cancer cells in comparison to mock treated cells. The above description of FIG. 1 regarding the columns, compounds, and y-axis equally apply to this Figure.
Figure 9:
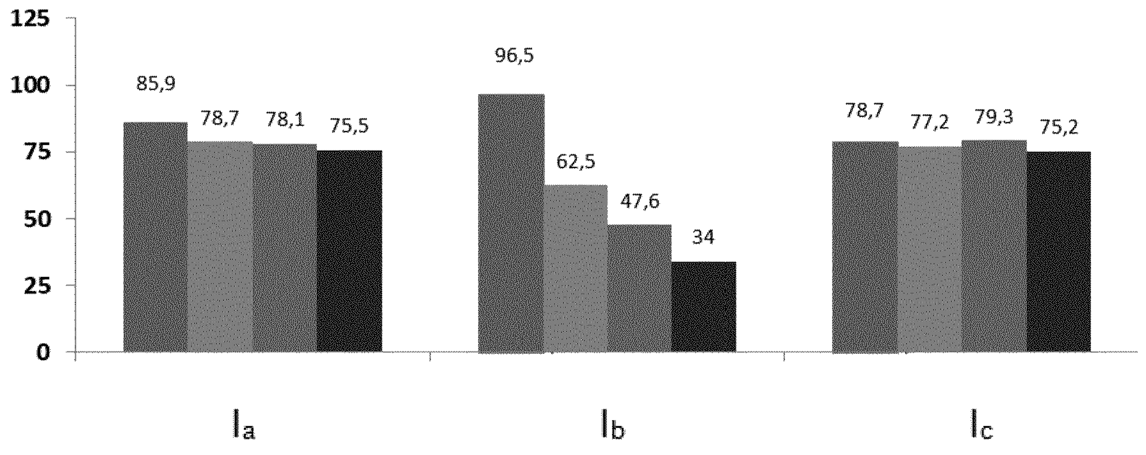
FIG. 9, is a bar diagram showing the inhibitory effect of various compounds of the invention on the growth of COLO668 human lung cancer cells in comparison to mock treated cells. The above description of FIG. 1 regarding the columns, compounds, and y-axis equally apply to this Figure.
Figure 10:
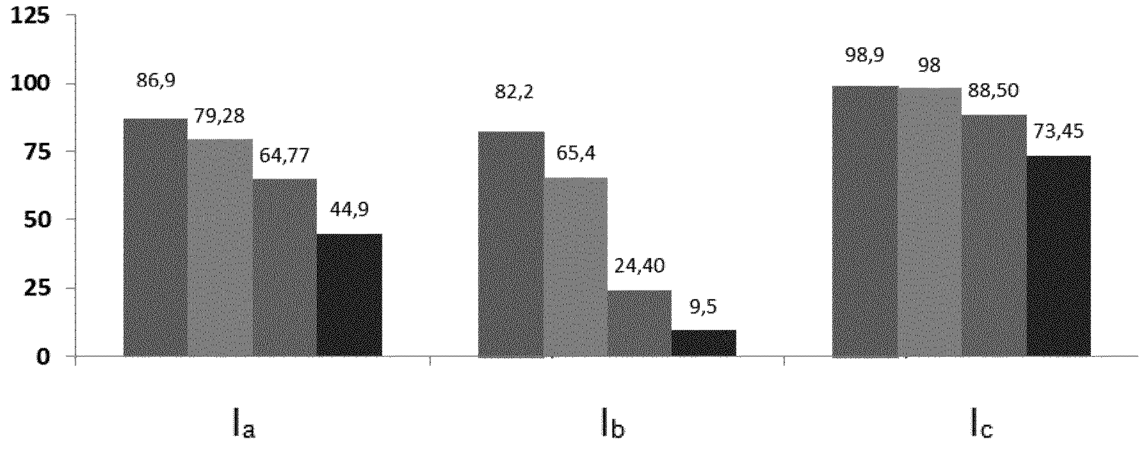
FIG. 10, is a bar diagram showing the inhibitory effect of various compounds of the invention on the growth of BXPC3 human pancreatic cancer cells in comparison to mock treated cells. The above description of FIG. 1 regarding the columns, compounds, and y-axis equally apply to this Figure.
Figure 11:
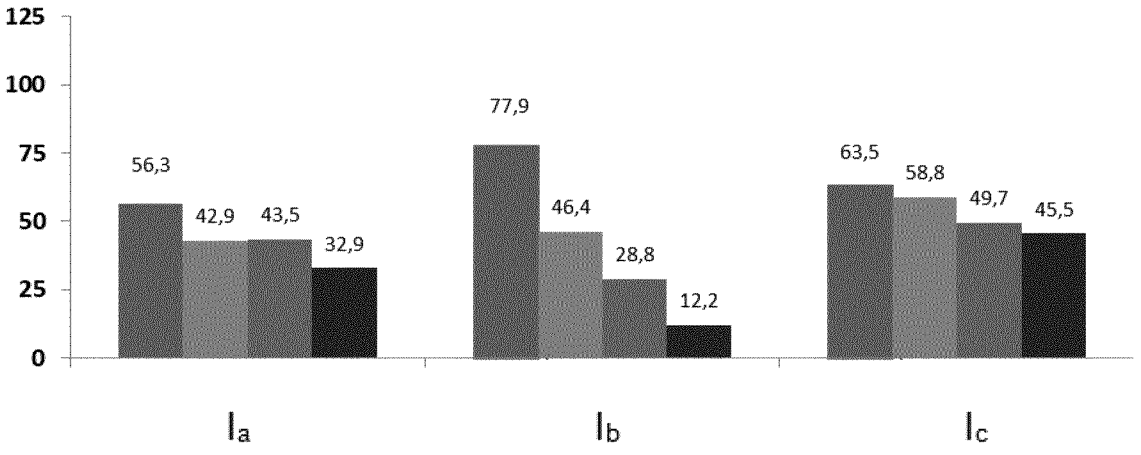
FIG. 11, is a bar diagram showing the inhibitory effect of various compounds of the invention on the growth of CAPAN2 human pancreatic cancer cells in comparison to mock treated cells. The above description of FIG. 1 regarding the columns, compounds, and y-axis equally apply to this Figure.
Figure 12:
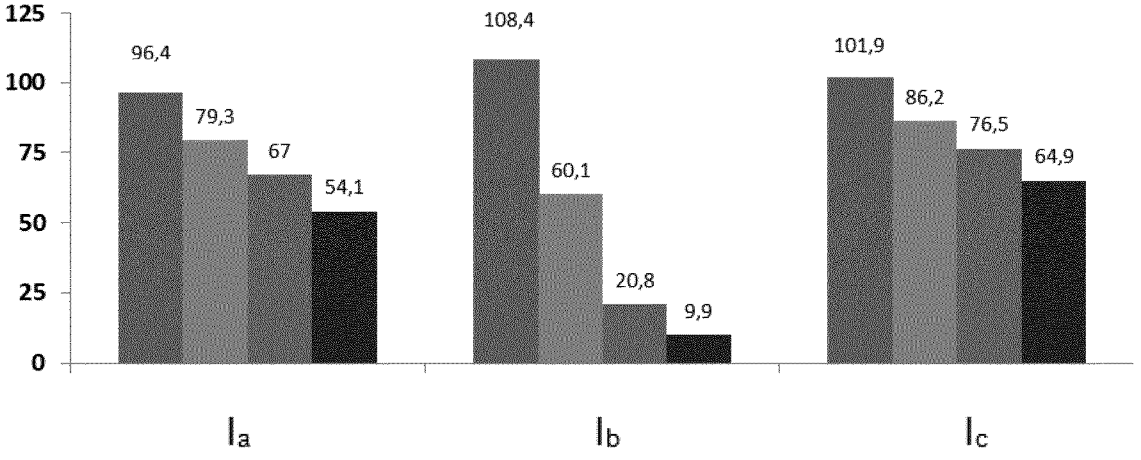
FIG. 12, is a bar diagram showing the inhibitory effect of various compounds of the invention on the growth of RWP1 human pancreatic cancer cells in comparison to mock treated cells. The above description of FIG. 1 regarding the columns, compounds, and y-axis equally apply to this Figure.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

As described above, the present invention provides ascorbic acid esters of formula (I) or a pharmaceutically acceptable salt thereof or a stereoisomer thereof or mixture of stereoisomers, with potent cancer inhibitory activity.

As used herein, the term "pharmaceutically acceptable salt", when referred to the compound of the invention, refers to those salts which are, within the scope of sound medical judgment, suitable for use in contact with the tissues of humans and non-human animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of the amino or thiol group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Compounds referred have an asymmetric centers and, therefore, exist in different isomeric forms. All single optical isomers and stereoisomers of the compounds referred to herein, and mixtures thereof, are considered within the scope of the present invention. Thus, any given compound referred to herein is intended to represent any one of a racemate, one or more stereisomeric forms, one or more atropisomeric forms, and mixtures thereof.

In the present invention the term "alkyl" encompasses both lineal and branched hydrocarbon chains. In a particular embodiment, optionally in combination with any of the embodiments provided above or below, "alkyl" refers to lineal hydrocarbon chains.

Illustrative non-limitative examples of "alkyl" are: methyl ($C_1$), ethyl ($C_2$), propyl ($C_3$), isopropyl ($C_3$), isobutyl ($C_4$), sec-butyl ($C_4$), tert-butyl ($C_4$), pentyl ($C_5$), hexyl ($C_6$), heptyl ($C_7$), octyl ($C_8$), nonyl ($C_9$), and decyl ($C_{10}$), among others.

In a particular embodiment of the first aspect, optionally in combination with any embodiments provided above or below, n is from 0 to 10, from 1 to 5, or from 2 to 3. In an even more particular embodiment, n is 1, or alternatively, n is 2.

In another particular embodiment of the first aspect, optionally in combination with any embodiments provided above or below, $R_1$ is $CH_2$ or O. As shown in the examples below, compounds where $R_1$ is $CH_2$ are particularly advantageous in the treatment of cancer.

In another particular embodiment of the first aspect, optionally in combination with any embodiments provided above or below, $R_2$ is selected from the group consisting of ($C_4$-$C_{12}$)alkyl, ($C_4$-$C_9$)alkyl, ($C_5$-$C_8$)alkyl or ($C_5$-$C_7$)alkyl. In an even more particular embodiment, $R_2$ is ($C_5$)alkyl.

In another particular embodiment of the first aspect, optionally in combination with any embodiments provided above or below, n is 2; $R_1$ is selected from the group consisting of $CH_2$, O, NH and S; and $R_2$ is ($C_3$-$C_{15}$)alkyl.

In another particular embodiment of the first aspect, optionally in combination with any embodiments provided above or below, n is 2, $R_1$ is $CH_2$, and $R_2$ is ($C_5$)alkyl. In another particular embodiment, n is 2, $R_1$ is O, and $R_2$ is ($C_5$)alkyl. In yet another particular embodiment, n is 2, $R_1$ is O, and $R_2$ is ($C_5$)alkyl. In yet another particular embodiment, n is 0, $R_1$ is O, and $R_2$ is ($C_5$)alkyl.

The most preferred compounds are those selected from Table 1:

TABLE 1

| Compound (I) | $R_1$ | $R_2$ | n |
|---|---|---|---|
| $I_a$ | O | ($C_5$)alkyl | 2 |
| $I_b$ | $CH_2$ | ($C_5$)alkyl | 2 |
| $I_c$ | O | ($C_8$)alkyl | 2 |
| $I_d$ | O | ($C_5$)alkyl | 0 |
| $I_e$ | O | ($C_5$)alkyl | 1 |
| $I_f$ | $CH_2$ | ($C_5$)alkyl | 1 |

Compounds of the invention may be easily prepared in a flexible manner from commercial reagents by a variety of methods.

Scheme I illustrates a particular embodiment of the process for the preparation of symmetrical compounds of formula (I):

Scheme I

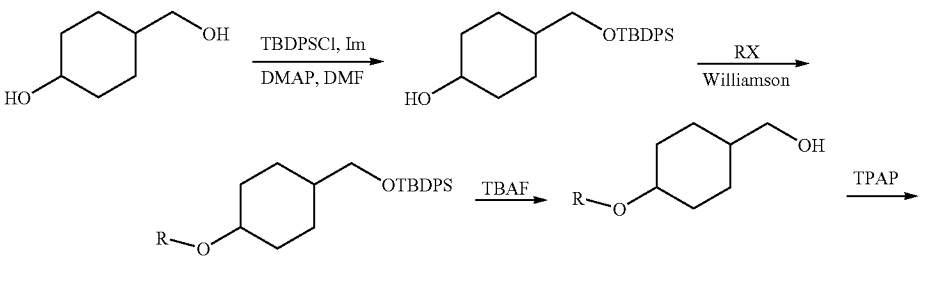

-continued

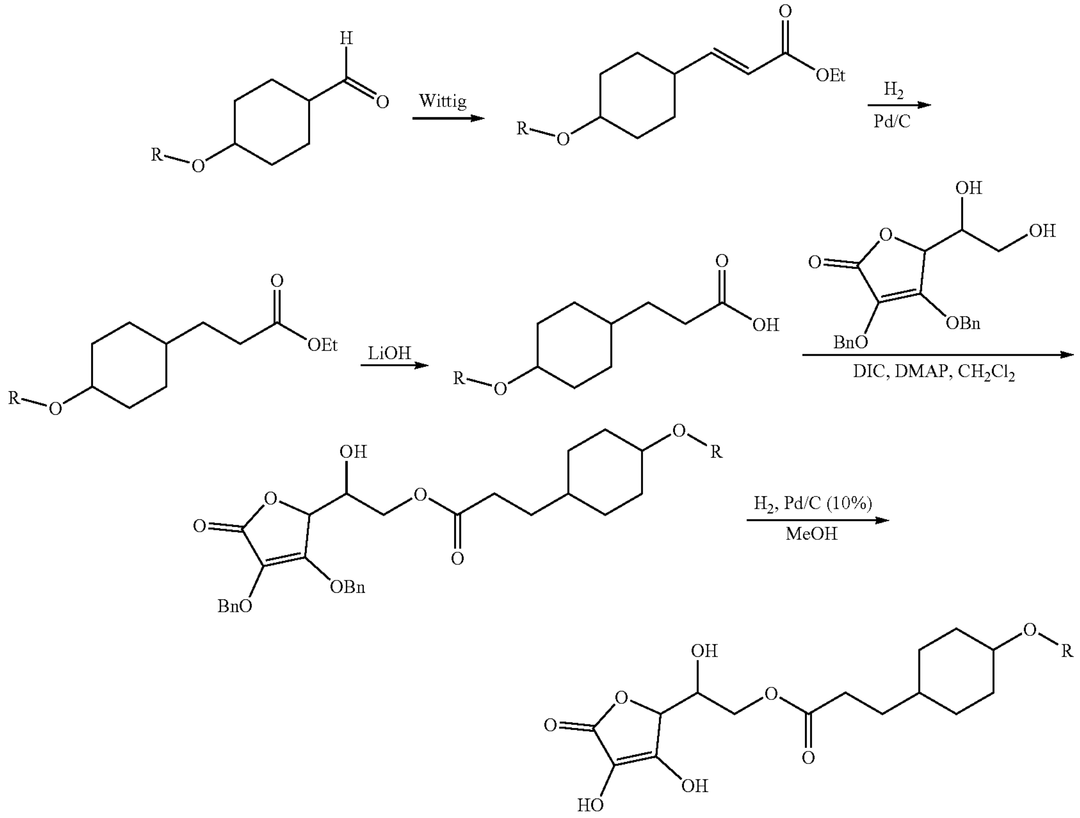

In the previous scheme, R is a ($C_3$-$C_{15}$)alkyl radical.

The preparation of pharmaceutically acceptable salts of the compounds of formula (I) can be carried out by methods known in the art. For instance, they can be prepared from the parent compound, which contains a basic moiety (NH, SH, OH), by conventional chemical methods. Generally, such salts are, for example, prepared by reacting the free base forms of these compounds with a stoichiometric amount of the appropriate pharmaceutically acceptable acid in water or in an organic solvent or in a mixture of them.

As disclosed before, the invention also provides in a second aspect a pharmaceutical composition comprising a therapeutically effective amount of the compound of the invention with at least one pharmaceutically acceptable excipient, diluent or carrier.

The expression "pharmaceutical composition" encompasses both compositions intended for human as well as compositions for other non-human mammals (i.e. veterinarian compositions).

The expression "therapeutically effective amount" as used herein, refers to the amount of the compound that, when administered, is sufficient to prevent development of, or alleviate to some extent, one or more of the symptoms of the disease which is addressed (i.e. cancer). The particular dose of compound administered according to this invention will of course be determined by the particular circumstances surrounding the case, including the compound administered, the route of administration, the particular condition being treated, and the similar considerations.

The expression "pharmaceutically acceptable excipient, diluent, or carrier" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as colouring agents, coating agents, sweetening, and flavouring agents can be present in the composition, according to the judgment of the formulator.

The pharmaceutical compositions containing the compound of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As described above, a third aspect of the invention provides the compound or the pharmaceutical composition of the invention for use as a medicament.

As described before, in a fourth aspect the present invention provides the compound or the pharmaceutical composition of the invention for use in the treatment or prevention of a neoplastic disease. Without wishing to be bound by theory, the compounds of the invention specifically target cancer cells because of the metabolic changes that occur in these cells. Therefore, the compounds of the invention may be useful for treating any kind of cancer, including non-solid tumors, such as leukemia.

The term "treating", "to treat" or "treatment", include without limitation restraining, slowing, stopping, reducing, ameliorating, or reversing the progression or severity of an existing symptom, clinical sign, disorder, condition, or disease. A treatment may be applied or administered therapeutically.

The term "preventing", "to prevent" or "prevention", include without limitation decreasing, reducing or ameliorating the risk of a symptom, clinical sings, disorder, condition, or disease, and protecting a subject from a symptom, clinical signs, disorder, condition, or disease. A prevention may be applied or administered prophylactically.

This aspect can also be formulated as the use of the compound or the pharmaceutical composition of the invention for the manufacture of a medicament for the treatment or prevention of a neoplastic disease. This aspect can also be formulated as a method for treating or preventing a neoplastic disease, the method comprising administering a therapeutically effective amount of the compound of the invention together with pharmaceutically acceptable excipients or carriers to a subject in need thereof.

As used herein, the term "neoplastic disease" refers to cancers of any kind and origin and precursor stages thereof. Illustrative non-limiting examples of neoplastic diseases which can be treated with the compound, conjugate and pharmaceutical composition of the invention include, although they are not limited to, papillomas, adenomas, lipomas, osteomas, myomas, angiomas, nevi, mature teratomas, carcinomas, sarcomas. immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, gastric cancer, pancreatic cancer, kidney cancer, esophageal cancer, hepatocarcinoma, head and neck cancer, etc. The term neoplastic disease is meant to encompass both primary and metastatic tumours.

In a particular embodiment of the fourth aspect, optionally in combination with any of the embodiments provided above or below, the neoplastic disease is selected from the group consisting of pancreatic cancer, melanoma, colon cancer, gastric cancer, and lung cancer. More particularly, the neoplastic disease is pancreatic cancer.

Compounds of the present invention can be used in the same manner as other known chemotherapeutic agents. Furthermore, they may be used alone or in combination with other suitable anticancer agents. Examples of anticancer agents include, but are limited to, chemotherapeutic agents, growth inhibitory agents, cytotoxic agents, agents used in radiation therapy, anti-angiogenesis agents, anti-lymphangiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA VEGF, or VEGF receptor(s), TRAIL/Apo2, and other bioactive and organic chemical agents, etc. Combinations thereof are also included in the invention.

As described above, in a fifth aspect the invention provides a preparation process of a compound of formula (I) as defined in the first aspect.

Examples of hydroxyl protective group can be found in T. W. Greene and P. G. M. Wuts, "Protective Groups in Organic Synthesis", Chapter 2, Protection for the Hydroxyl Group, Including 1,2- and 1,3-Diols, John Wiley & Sons, Inc., 1999, pp. 17-245.

Representative hydroxyl protective groups include those in which the hydroxyl group is acylated or alkylated, such as phenylmethyl and triethyl ethers, as well as alkyl ethers, tetrahydropyranyl ethers, trialkyl ethers, such as tert-butyl dimethyl silyl (TBS), tert-butyl diphenyl (TBDPS), allyl ethers, and benzyl esters.

In a particular embodiment of the fifth aspect, optionally in combination with any of the embodiments provided above or below, the protecting group (PG) is benzyl ester.

The introduction and removal of the protective group can be carried out by methods known in the technique (c.f. T. W. Greene et al.) The specific conditions depend on the protective group used. In a particular application, when a Bn group is used, it can be introduced by reaction with bencyl bromide in the presence of a suitable solvent. Deprotection may take place by reaction with Pd/C in methanol.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1: Preparation of (R)-3,4-bis(benzyloxy)-5-((S)-2,2-dimethyl-1,3-dioxolan-4-yl)furan-2 (5H)-one (Compound 2)

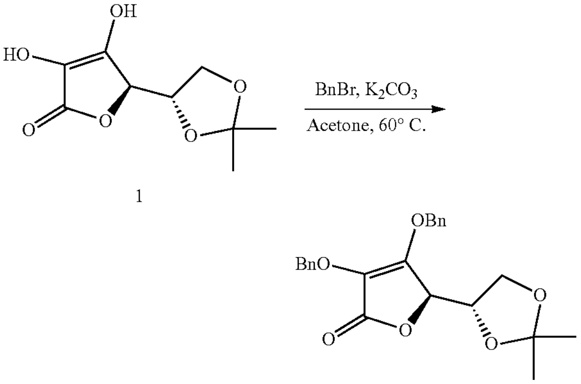

1

2

Compound 1 (5.55 g, 25.6 mmol) and $K_2CO_3$ powder (10.6 g, 77 mmol) were suspended in acetone (80 ml). After reflux (60° C.), bencyl bromide (mg, mmol) was added and the mixture was allowed to reflux for another 16 h. The solvent was removed under reduced pressure. The residue was purified by column chromatography with ethylacetate-hexane (20%) to give compound 2 (8.14 g, 80%). Compound 2: Colourless oil, Rf: 0.67 (70% ethylacetate/hexane). IR (ATR, $cm^{-1}$): 1763, 1677, 1316, 1213, 1148, 1068. EM (ESI) [m/z, (%)]: 419.14 ($M^+$+Na, 13), 397.16 ($M^+$+1, 100). EMAR (ESI): 397.1646 calculated for $C_{23}H_{25}O_6$ and found 397.1651.

Example 2: Preparation of (R)-3,4-bis(benzyloxy)-5-((S)-1,2-dihydroxyethyl)furan-2(5H)-one (Compound 3)

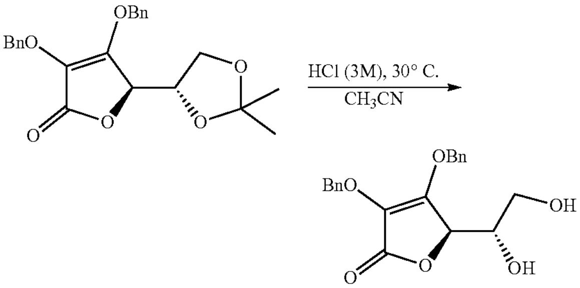

Compound 2 (5.9 g, 14.9 mmol) was dissolved in $CH_3CN$ (240 ml), then the aqueous solution of HCl 3M (20 ml) was added and the reaction mixture was stirred for 2 h. at 30° C. The solvent was removed under reduced pressure and the residue was diluted in EtOAc. The organic layer was washed successively with brine, then was dried over anhydrous $Na_2SO_4$, filtered and concentrated under reduced pressure. The residue was purified by column chromatography with ethylacetate-hexane (60%) to give compound 3 (5.2 g, 98%). Compound 3: Colourless oil, Rf: 0.17 (70% ethylacetate/hexane). IR (ATR, $cm^{-1}$): 3391, 2925, 1748, 1666, 1317, 1152, 1067, 697. EM (ESI) [m/z, (%)]: 379.11 ($M^{+}$+Na, 5), 357.13 ($M^{+}$+1, 100). EMAR (ESI): 357.1333 calculated for $C_{20}H_{21}O_6$ and found 357.1333.

Example 3. Preparation of 4-(((tert-butyldiphenylsilyl)oxy)methyl)cyclohexan-1-ol (Compound 5)

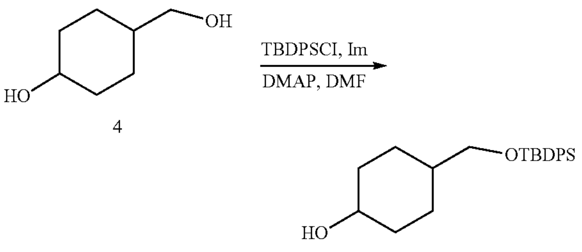

4

5

To a solution of diol 4 (910 mg, 6.99 mmol) in DMF (15 mL) were added Imidazole (1.9 g, 28 mmol), a catalytic amount of DMAP and TBDPSCl (2 ml, 7.69 mmol) and the mixture was stirred for 2 h. at room temperature. The solvent was evaporated, $H_2O$ (10 mL) added and the product extracted with $CH_2Cl_2$ (3×10 mL). The organic layer was dried over $Na_2SO_4$, filtered and the solvent evaporated under reduced pressure. The residue was purified by column chromatography with ethylacetate-hexane (30%) to give compound 5 (2.4 g, 93%). Compound 5: Colourless oil, Rf: 0.85 (50% ethylacetate/hexane). IR (ATR, $cm^{-1}$): 3350, 2927, 2859, 1427, 1110, 701. EM (ESI) [m/z, (%)]: 369.22 ($M^{+}$+1, 100), 351.21 ($M^{+}$-OH, 21). EMAR (ESI): 369.2244 calculated for $C_{23}H_{33}O_2Si$ and found 369.2241.

Example 4. Preparation of tert-butyl((4-(pentyloxy)cyclohexyl)methoxy)diphenylsilane (Compound 6)

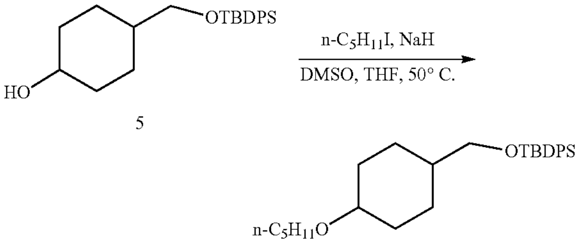

5

6

To a solution of compound 5 (9.3 g, 25.2 mmol) in THF (90 ml) and DMSO (12 ml) was added NaH (60%) (3.02 g, 75.6 mmol) at 0° C. and the mixture was cooled to 50° C. After 30 min, iodopentane (11.5 ml, 88.2 mmol) was added and the mixture was allowed to reflux for another 21 h. The reaction was quenched with $H_2O$ (20 mL) and it was extracted with AcOEt (3×20 mL). The organic layer was dried over $Na_2SO_4$, filtered and the solvent evaporated under reduced pressure. The residue was purified by column chromatography with ethylacetate-hexane (3%) to give compound 6 (3.81 g, 35%) and ethylacetate-hexane (30%) to give compound 5 (Starting Material) (5.45 g, 50%). Compound 6: Colourless oil, Rf: 0.95 (20% ethylacetate/hexane). IR (ATR, $cm^{-1}$): 2929, 2856, 1427, 1109, 701. EM (ESI) [m/z, (%)]: 439.30 ($M^{+}$+1, 7), 361.25 (100), 183.17 ($M^{+}$-OTBDPS, 68). EMAR (ESI): 439.3026 calculated for $C_{28}H_{43}O_2Si$ and found 439.2694.

Example 5. Preparation of (4-(pentyloxy)cyclohexyl)metanol (Compound 7)

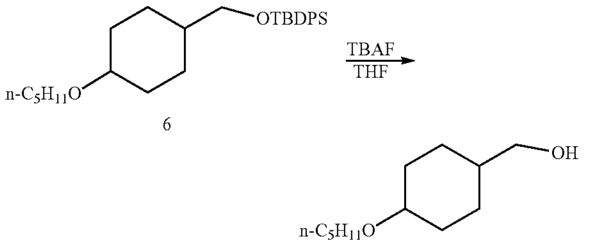

6

7

To a solution of 6 (3.79 g, 8.63 mmol) in THF (20 mL) was added a 1.0 M solution of TBAF (17 mL, 17 mmol) at room temperature and the mixture was stirred for 16 h. in the same conditions. The solvent was evaporated and the residue was chromatographed on silica gel using ethylacetate-hexane (30%) as eluent affording compound 7 (1.28 g, 75%).

Compound 7: Colourless oil, Rf: 0.42 (30% ethylacetate/hexane). IR (ATR, $cm^{-1}$): 3371, 2928, 2857, 1451, 1090, 1036. EM (ESI) [m/z, (%)]: 201.18 ($M^{+}$+1, 45), 183.17 ($M^{+}$-OH, 100). EMAR (ESI): 201.1849 calculated for $C_{12}H_{25}O_2$ and found 201.1847.

Example 6. Preparation of ethyl (E)-3-(4-(pentyloxy)cyclohexyl)acrylate (Compound 8)

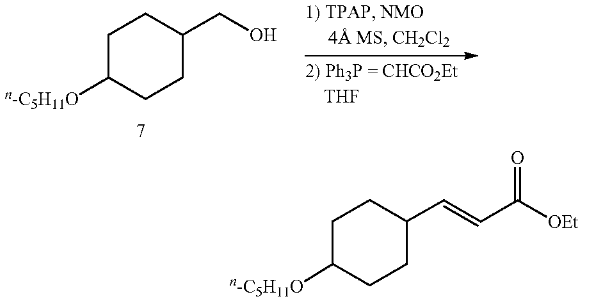

7

8

To a solution of compound 7 (1.13 g, 5.64 mmol) in $CH_2Cl_2$ (20 ml) were added molecular sieves (850 mg), NMO (1.98 g, 16.9 mmol) and a catalitic amount of TPAP and stirring was continued at room temperature for 1 h. The reaction was filtered under celite. The solvent was evaporated and the residue was dissolved in THF (10 ml) and $Ph_3P{=}CHCO_2Et$ (3.94 g, 11.3 mmol) added, the mixture was stirred for 2 days. The solvent was evaporated and the residue was chromatographed on silica gel using ethylacetate-hexane (5%) as eluent affording compound 8 (787 mg, 52%). Compound 8: Colourless oil, Rf: 0.68 (10% ethylacetate/hexane). IR (ATR, $cm^{-1}$): 2931, 2858, 1720, 1652, 1267, 1173, 1096. EM (ESI) [m/z, (%)]: 269.21 ($M^{+}$+1, 52), 223.16 (33), 181.12 (100). EMAR (ESI): 269.2111 calculated for $C_{16}H_{29}O_3$ and found 269.2107.

Example 7. Preparation of 3-(4-(pentyloxy)cyclohexyl)propanoic acid (Compound 9)

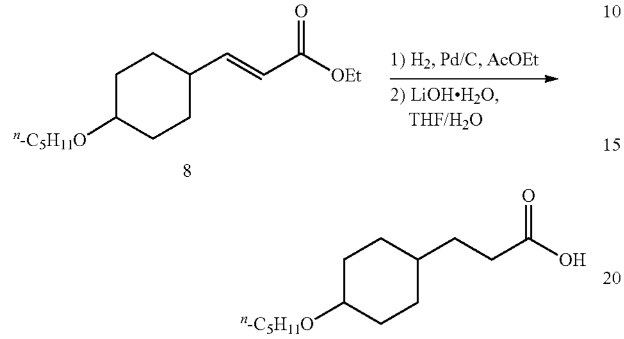

8

9

To a mixture of compound 8 (450 mg, 1.67 mmol) in ethylacetate (15 mL) was added a catalytic amount of Pd/C (10%) and the suspensión was stirred for 14 h. at room temperature under $H_2$. The mixture was then filtered through celite and the filtrate was rotatory evaporated. The residue was dissolved in THF/$H_2O$ (1:1, 7 ml) and LiOH. $H_2O$ added, the mixture was stirred for 18 h. The solvent was evaporated and the residue was chromatographed on silica gel using ethylacetate-hexane (30%) as eluent affording compound 9 (360 mg, 89%). Compound 9: Colourless oil, Rf: 0.45 (20% ethylacetate/hexane). IR (ATR, $cm^{-1}$): 3031, 2927, 2856, 2782, 1707, 1453, 1089. EM (ESI) [m/z, (%)]: 397.33 (100), 243.19 ($M^+$+1, 67). EMAR (ESI): 243.1954 calculated for $C_{14}H_{27}O_3$ and found 243.1951.

Example 8. Preparation of(S)-2-((R)-3,4-bis(benzyloxy)-5-oxo-2,5-dihydrofuran-2-yl)-2-hydroxyethyl 3-(4-(pentyloxy)cyclohexyl)propanoate (Compound 10)

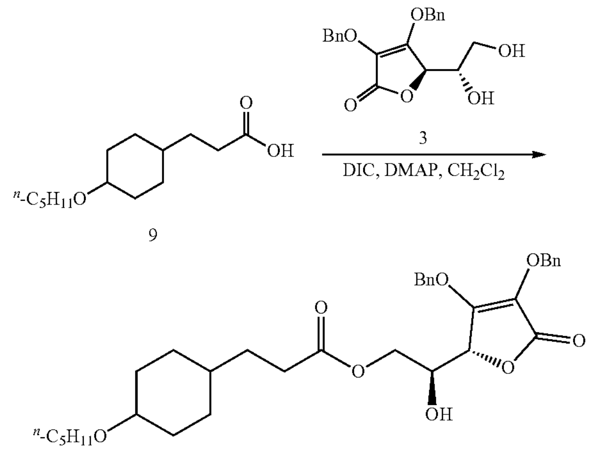

3

9

10

To a stirred solution of compound 9 (172 mg, 0.70 mmol) in $CH_2Cl_2$ (5 ml) was added DIC (120 μl, 0.77 mmol) and DMAP (72 mg, 0.70 mmol) and the mixture was stirred for 30 min. Protected vitamin C 3 (379 mg, 1.06 mmol) was added dropwise in $CH_2Cl_2$ (4 ml) and the reaction mixture was stirred overnight at room temperature and then filtrated. The filtrate was concentrated under reduced pressure. The residue was purified by column chromatography with ethylacetate-hexane (12%) to give compound 10 (193 mg, 48%).

Compound 10: Colourless oil, Rf: 0.43 (30% ethylacetate/hexane). IR (ATR, $cm^{-1}$): 3415, 2926, 2856, 1765, 1742, 1674, 1454, 1320, 1153. EM (ESI) [m/z, (%)]: 581.30 ($M^+$+1, 100). EMAR (ESI): 581.3108 calculated for $C_{34}H_{45}O_8$ and found 581.3083.

Example 9: Preparation of 2-(3,4-dihydroxy-5-oxo-2,5-dihydrofuran-2-yl)-2-hydroxyethyl 3-(4-(pentyloxy)cyclohexyl)propanoate (Compound Ia)

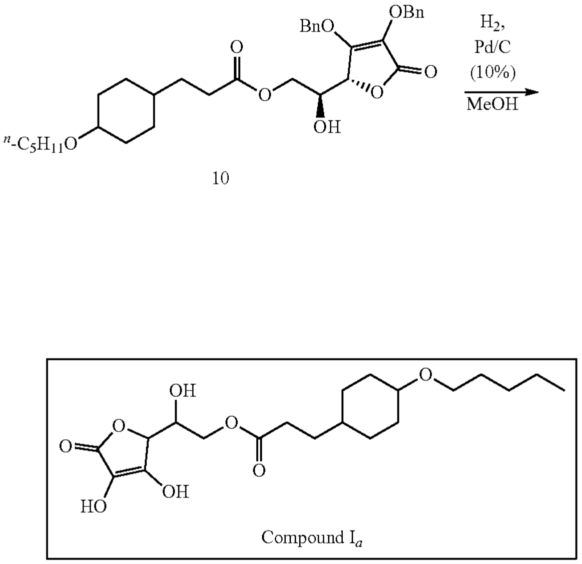

10

Compound $I_a$

To a mixture of compound 10 (193 mg, 0.33 mmol) in methanol (10 ml) was added a catalytic amount of Pd/C (10%) and the suspension was stirred for 14 h. at room temperature under $H_2$. The mixture was then filtered through celite and the filtrate was rotatory evaporated, affording compound Ia (131 mg, 98%). Compound Ia: Colourless oil, Rf: 0.10 (ethylacetate). IR (ATR, $cm^{-1}$): 3367, 2925, 2854, 1740, 1668, 1346, 1116. $^1$H-RMN (MeOD-$d_4$, δ): 4.75 (d, J=2.1 Hz, 1H, H-4), 4.25 (m, 2H, H-6), 4.11 (m, 2H, H-5), 3.49 (m, 1H, H-7'), 3.41 (t, J=6.5 Hz, 2H, H-8'), 2.41 (t, J=7.7 Hz, 2H, H-2'), 1.92 (m, 3H), 1.52 (m, 4H), 1.36 (m, 9H), 0.93 (m, 3H) ppm. $^{13}$C-RMN (MeOD-$d_4$, θ): 174.0 (C-1'), 173.9 (C-1'), 171.7 (C-1), 152.6 (C-3), 118.7 (C-2), 78.3 (CH-7'), 75.8 (CH), 73.9 (CH-7'), 67.9 ($CH_2$-8), 67.5 ($CH_2$-8), 66.7 (CH), 64.5 ($CH_2$-6), 36.5 (CH-4), 35.9 (CH-4), 31.8 ($CH_2$), 31.4 ($CH_2$), 31.3 ($CH_2$), 31.2 ($CH_2$), 31.1 ($CH_2$), 30.6 ($CH_2$), 29.5 ($CH_2$), 29.0 ($CH_2$), 28.3 ($CH_2$), 28.1 ($CH_2$), 26.8 ($CH_2$), 22.2 ($CH_2$), 22.2 ($CH_2$), 13.2 ($CH_3$-12'), 13.1 ($CH_3$-12') ppm. EM (ESI) [m/z, (%)]: 401.21 ($M^+$+1, 100), 369.31 (35). EMAR (ESI): 401.2169 calculated for $C_{20}H_{33}O_8$ and found 401.2155.

Example 10. Preparation of 4-(((tert-butyldiphenylsilyl)oxy)methyl)cyclohexan-1-ol (Compound 2)

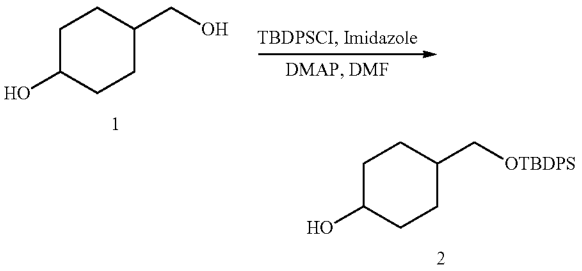

1
2

To a solution of compound 1 (5.0 g, 0.03 mol) in DMF (100 mL) were added Imidazole (10.5 g, 0.15 mol), a catalytic amount of DMAP and TBDPSCl (10.5 ml, 0.04 mol) and the mixture was stirred for 4 h. at room temperature. The solvent was evaporated, ethylacetate (20 mL) added and the product washed with $H_2O$ (3x20 mL). The organic layer was dried over $Na_2SO_4$, filtered and the solvent evaporated under reduced pressure. The residue was purified by column chromatography with ethylacetate-hexane (15%) to give compound 2 (13.9 g, 99%). Compound 2: Colourless oil, Rf: 0.60 (30% ethylacetate/hexane). IR (ATR, $cm^{-1}$): 3350, 2927, 2859, 1427, 1110, 701. MS (ESI) [m/z, (%)]: 369 ([$M^+$+1], 100), 351 ([$M^+$-OH], 21). HR-MS (ESI): 369.2244 calculated for $C_{23}H_{33}O_2Si$ and found 369.2241.

Example 11. Preparation of ethyl (E)-3-((4-(((tert-butyldiphenylsilyl)oxy)methyl)cyclohexyl)oxy)acrylate (Compound 3)

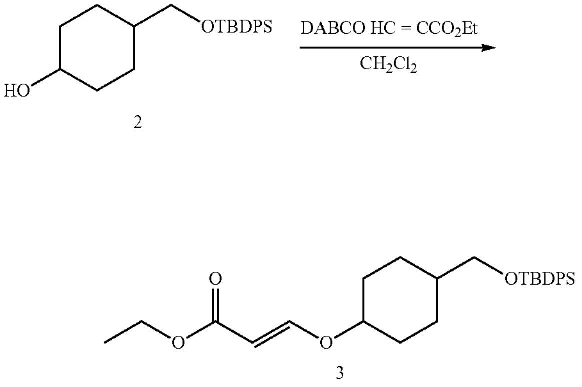

2
3

To a solution of 2 (372 mg, 1.01 mmol) and DABCO (23 mg, 0.20 mmol) in $CH_2Cl_2$ (8 mL) was added $HCCCO_2Et$ (154 µL, 1.50 mmol) at room temperature and the mixture was stirred for 10 h. The solvent was evaporated and the residue was chromatographed on silica gel using ethylacetate-hexane (5%) as eluent affording compound 3 (420 mg, 90%). Compound 3: Colourless oil, Rf: 0.67 (30% ethylacetate/hexane). IR (ATR, $cm^{-1}$): 2931, 2899, 2857, 1706, 1640. MS (ESI) [m/z, (%)]: 467 ([$M^+$+1], 100), 425 (26), 352 (23), 351 (76). HR-MS (ESI): 467.2612 calculated for $C_{28}H_{39}O_4Si$ and found 467.2614.

Example 12. Preparation of compound ethyl 3-((4-(((tert-butyldiphenylsilyl)oxy)methyl)cyclohexyl)oxy)propanoate (Compound 4)

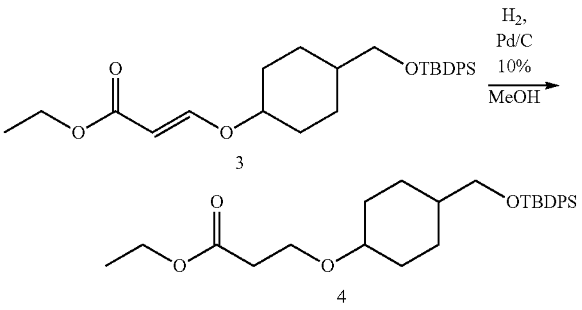

3
4

To a mixture of compound 3 (295 mg, 0.63 mmol) in MeOH (5 mL) was added a catalytic amount of Pd/C (10%) and the suspension was stirred for 24 h. at room temperature under $H_2$. The mixture was then filtered through celite and the filtrate was rotatory evaporated. The organic layer was dried over $Na_2SO_4$, filtered and the solvent evaporated under reduced pressure to give compound 4 (292 mg, 99%). Compound 4: Colourless oil, Rf: 0.63 (30% ethylacetate/hexane). IR (ATR, $cm^{-1}$): 2929, 2894, 2856, 1735. MS (ESI) [m/z, (%)]: 469 ([$M^+$+1], 36), 467 (13), 391 (46), 351 (56), 349 (45), 144 (100). HR-MS (ESI): 469.2769 calculated for $C_{28}H_{41}O_4Si$ and found 469.2775.

Example 13. Preparation of compounds 3-((4-(((tert-butyldiphenylsilyl)oxy)methyl)cyclohexyl)oxy)propanal (Compound 5) and 3-((4-(((tert-butyldiphenylsilyl)oxy)methyl)cyclohexyl)oxy)propan-1-ol (Compound 6)

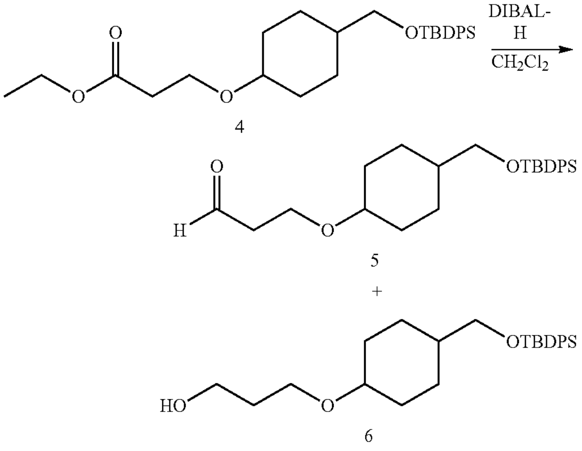

4
5
+
6

To a solution of a compound 4 (352 mg, 0.75 mmol) in $CH_2Cl_2$ (7 mL) at −78° C., was added a 1.0 M solution of DIBAL-H in hexane (1.1 mL, 1.13 mmol) and the reaction mixture was stirred for 30 min. $^t$BuOMe (10 mL) and $H_2O$ (300 µL) were added, vigorous stirring was maintained until the formation of an off-white gel. Next, a 4N solution of NaOH (300 µL), $H_2O$ (300 µL) was added and the stirring was prolonged until the formation of a white solid. The organic layer was dried over $Na_2SO_4$, filtered and the solvent evaporated under reduced pressure. The residue was purified by column chromatography with ethylacetate-hexane (5%) to give compound 5 (285 mg, 90%) and 6 (28 mg, 9%). Compound 5: Colourless oil, Rf: 0.50 (20% ethylacetate/hexane). IR (ATR, $cm^{-1}$): 2929, 2896, 2856, 1725. MS (ESI) [m/z, (%)]: 447 ([$M^+$+Na], 31), 426 ([$M^+$+2], 31), 425 ([$M^+$+1], 88), 351 (100), 347 (80). HR-MS (ESI): 447.2326 calculated for $C_{26}H_{36}NaO_3Si$ and found 447.2324. Compound 6: Colourless oil, Rf: 0.17 (20% ethylacetate/hexane). IR (ATR, $cm^{-1}$): 3411, 2927, 2889, 2855. MS (ESI) [m/z, (%)]: 449 ([$M^+$+Na], 4), 391 (12), 349 ([$M^+$-Ph], 100), 237 (29). HR-MS (ESI): 449.2482 calculated for $C_{26}H_{38}NaO_3Si$ and found 449.2494.

Example 14. Preparation of Compound (E)-tert-butyl((4-(oct-3-en-1-yloxy)cyclohexyl)methoxy)diphenylsilane (Compound 7)

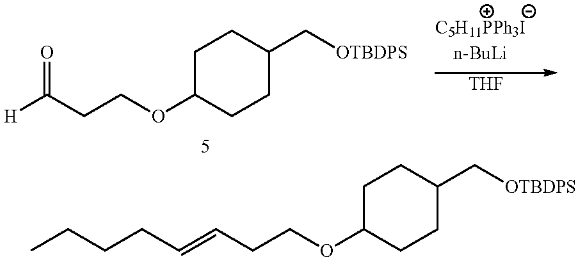

5

7

On the suspension of $IPh_3PC_5H_{11}$ (842 mg, 1.83 mmol) in THF (10 ml) cooled to 0° C. was added a 2.5 M solution of n-BuLi (731 µL, 1.83 mmol), the mixture was stirred for 1 h. Compound 5 (195 mg, 0.46 mmol) in THF (3 mL) was added and stirring was continued at room temperature for 7.5 h. The reaction was quenched with a saturated solution of $NaHCO_3$ (20 mL) and it was extracted with ethylacetate (3x15 mL). The organic layer was dried over $Na_2SO_4$, filtered and the solvent evaporated under reduced pressure. The residue was purified by column chromatography with ethylacetate-hexane (2%) to give compound 7 (170 mg, 78%). Compound 7: Colourless oil, Rf: 0.94 (20% ethylacetate/hexane). IR (ATR, $cm^{-1}$): 2948, 2933, 2889, 2854. MS (ESI) [m/z, (%)]: 479 ([$M^+$+1], 42), 351 (46), 280 (21), 279 (100). HR-MS (ESI): 479.3340 calculated for $C_{31}H_{47}O_2Si$ and found 479.3328.

Example 15. Preparation of tert-butyl((4-(octyloxy)cyclohexyl)methoxy)diphenylsilane (Compound 8)

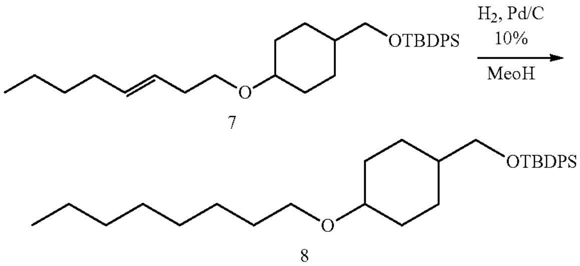

7

8

To a mixture of compound 7 (90 mg, 0.19 mmol) in MeOH (5 mL) was added a catalytic amount of Pd/C (10%) and the suspension was stirred for 24 h. at room temperature under $H_2$. The mixture was then filtered through celite and the filtrate was rotatory evaporated. The organic layer was dried over $Na_2SO_4$, filtered and the solvent evaporated under reduced pressure to give compound 8 (88 mg, 98%). Compound 8: Colourless oil, Rf: 0.93 (20% ethylacetate/hexane). IR (ATR, $cm^{-1}$): 2952, 2928, 2897, 2856. MS (ESI) [m/z, (%)]: 479 ([$M^+$+1], 42), 351 (46), 280 (21), 279 (100). HR-MS (ESI): 479.3340 calculated for $C_{31}H_{47}O_2Si$ and found 479.3328.

Example 16. Preparation of (4-(octyloxy)cyclohexyl)methanol (Compound 9)

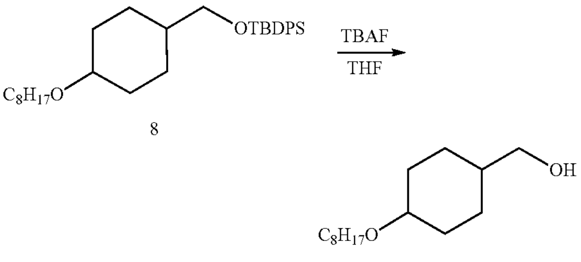

8

9

To a solution of compound 8 (420 mg, 0.87 mmol) in THF (5 mL) was added a 1.0 M solution of TBAF (1.3 mL, 1.31 mmol) at room temperature and the mixture was stirred for 24 h in the same conditions. The solvent was evaporated and the residue was chromatographed on silica gel using ethylacetate-hexane (10%) as eluent affording compound 9 (194 mg, 93%). Compound 9: Colourless oil, Rf: 0.28 (20% ethylacetate/hexane). IR (ATR, $cm^{-1}$): 3314, 2925, 2855, 1443. MS (ESI) [m/z, (%)]: 279 (23), 265 ([$M^+$+Na], 100), 227 (26), 225 (49). HR-MS (ESI): 265.2138 calculated for $C_{15}H_{30}NaO_2$ and found 265.2133.

Example 17. Preparation of 4-(octyloxy)cyclohexane-1-carbaldehyde (Compound 10)

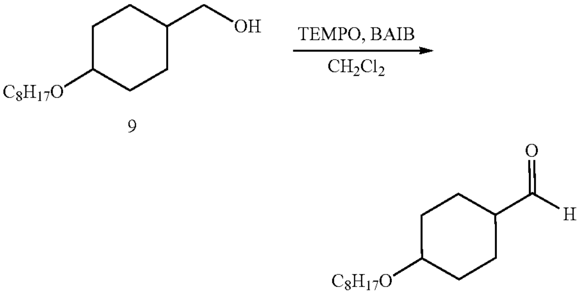

9

10

To a solution of compound 9 (194 mg, 0.80 mmol) in $CH_2Cl_2$ (5 ml) were added a catalytic amount of TEMPO, BAIB (387 mg, 1.20 mmol) and the mixture was stirred for 2 h. at room temperature. The solvent was evaporated, $^t$BuOMe (5 mL) added and the product washed with $Na_2S_2O_3$ 15% (3x10 mL) and a saturated solution of $NaHCO_3$ (3x10 mL). The solvent evaporated under reduced pressure and the residue was purified by column chromatography with ethylacetate-hexane (1%) to give compound 10 (173 g, 90%). Compound 10: Colourless oil, Rf: 0.67 (20% ethylacetate/hexane). IR (ATR, $cm^{-1}$): 2925, 2854, 1702, 1455, 1066. MS (ESI) [m/z, (%)]: 257 (100), 241 ([$M^+$+1], 4), 146 (22), 144 (46). HR-MS (ESI): 241.2162 calculated for $C_{15}H_{29}O_2$ and found 241.2142.

Example 18. Preparation of ethyl (E)-3-(4-(octyloxy)cyclohexyl)acrylate (Compound 11)

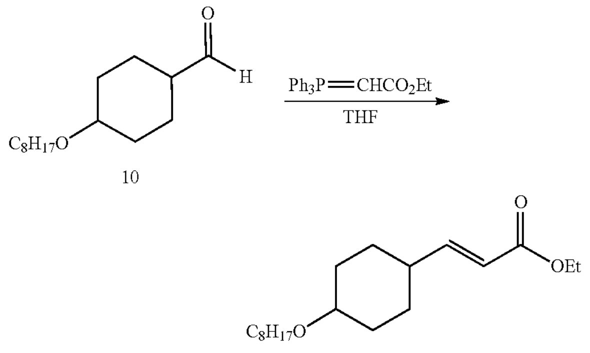

10

11

To a solution of compound 10 (165 mg, 0.68 mmol) in THF (5 ml), $Ph_3P{=}CHCO_2Et$ (479 mg, 1.37 mmol) was added, the mixture was stirred for 24 h at room temperature. The reaction was quenched with $H_2O$ (10 mL) and it was extracted with ethylacetate (3x10 mL). The organic layer was dried over $Na_2SO_4$, filtered and the solvent evaporated under reduced pressure. The residue was purified by column chromatography with ethylacetate-hexane (1%) to give compound 11 (153 mg, 72%). Compound 11: Colourless oil, Rf: 0.72 (20% ethylacetate/hexane). IR (ATR, $cm^{-1}$): 2927, 2855, 1721, 1652, 1465. MS (ESI) [m/z, (%)]: 312 (26), 311 ([$M^+$+1], 100), 181 (55), 146 (32), 144 (60), 131 (32). HR-MS (ESI): 311.2581 calculated for $C_{19}H_{35}O_3$ and found 311.2573.

Example 19. Preparation of 3-(4-(octyloxy)cyclohexyl)propanoic acid (Compound 12)

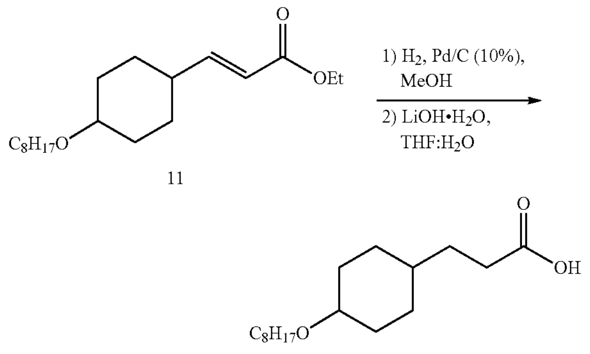

11

12

To a mixture of compound 11 (160 mg, 0.51 mmol) in MeOH (5 mL) was added a catalytic amount of Pd/C (10%) and the suspensión was stirred for 24 h. at room temperature under $H_2$. The mixture was then filtered through celite and the filtrate was rotatory evaporated. The residue was dissolved in THF/$H_2O$ (1:1, 8 ml) and LiOH. $H_2O$ (32 mg, 0.80 mmol) added, the mixture was stirred at room temperature for 23 h. HCl 10% (4 mL) added and the product was extracted with $CH_2Cl_2$ (3x5 mL). The organic layer was dried over $Na_2SO_4$, filtered and the solvent evaporated under reduced pressure. The residue was purified by column chromatography with ethylacetate-hexane (30%) to give compound 12 (137 mg, 95%). Compound 12: Colourless oil, Rf: 0.80 (50% ethylacetate/hexane). IR (ATR, $cm^{-1}$): 3461, 3001, 2925, 2854, 1709, 1455, 1275. MS (ESI) [m/z, (%)]: 302 (11), 285 ([$M^+$+1], 100), 155 (31), 144 (34). HR-MS (ESI): 285.2424 calculated for $C_{17}H_{33}O_3$ and found 285.2419.

Example 20. Preparation of(S)-2-((R)-3,4-bis(benzyloxy)-5-oxo-2,5-dihydrofuran-2-yl)-2-hydroxyethyl 3-(4-(octyloxy)cyclohexyl)propanoate (Compound 13)

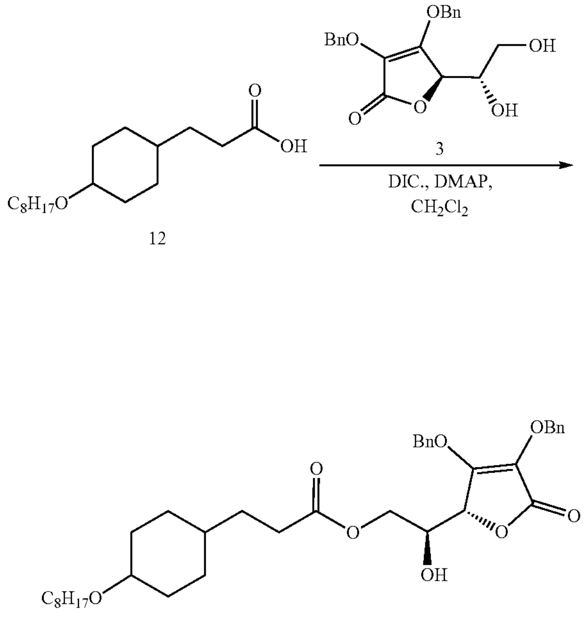

12

3

13

To a stirred solution of compound 12 (90 mg, 0.32 mmol) in $CH_2Cl_2$ (5 ml) was added DIC (44.0 μl, 0.35 mmol) and DMAP (33 mg, 0.32 mmol) and the mixture was stirred for 10 min. Protected vitamin C 3 (171 mg, 0.48 mmol) was added dropwise in $CH_2Cl_2$ (5 ml) and the reaction mixture was stirred 6 h at room temperature and then filtrated. The filtrate was concentrated under reduced pressure. The residue was purified by column chromatography with ethylacetate-hexane (10%) to give compound 13 (108 mg, 54%).

Compound 13: Colourless oil, Rf: 0.53 (30% ethylacetate/hexane). IR (ATR, $cm^{-1}$): 3404, 2925, 2853, 1767, 1743, 1673, 1454, 1320. MS (ESI) [m/z, (%)]: 640 (19), 623 ([$M^+$+1], 100), 411 (15), 146 (38), 144 (93), 131 (35). HR-MS (ESI): 623.3578 calculated for $C_{37}H_{51}O_8$ and found 623.3584.

Example 21. Preparation of 2-(3,4-dihydroxy-5-oxo-2,5-dihydrofuran-2-yl)-2-hydroxyethyl 3-(4-(octyloxy)cyclohexyl)propanoate (Compound $I_c$)

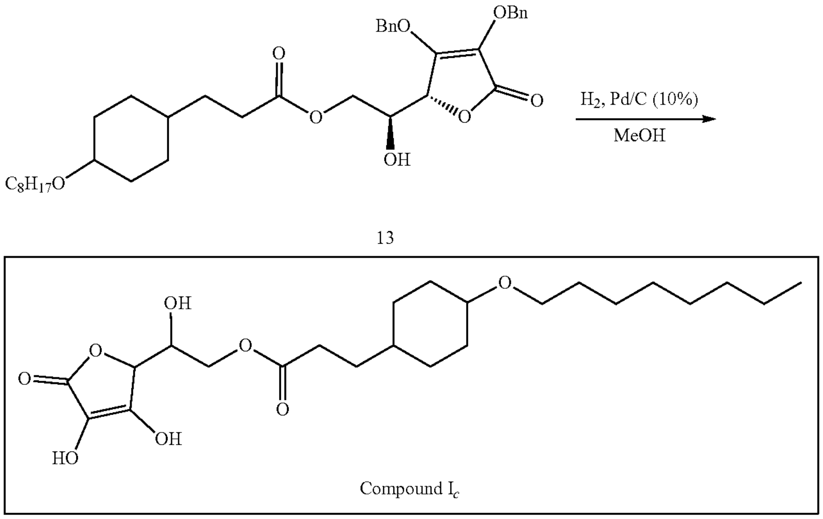

13

Compound $I_c$

To a mixture of compound 13 (104 mg, 0.17 mmol) in methanol (4 ml) was added a catalytic amount of Pd/C (10%) and the suspensiön was stirred for 5 h at room temperature under $H_2$. The mixture was then filtered through celite and the filtrate was rotatory evaporated, affording compound 14 (63 mg, 84%). Compound 14: Colourless oil, Rf: 0.10 (ethylacetate). IR (ATR, $cm^{-1}$): 3337, 2967, 2929, 2874, 1721, 1613, 1562, 1522.

$^1$H-NMR (MeOD-$d_4$, δ): 4.75 (m, 1H, CH-2"/3"), 4.16 (m, 3H, CH-2"/3", $CH_2$-1"), 3.49 (m, 1H, $CH_2$-1'/CH-7), 3.41 (t, J=6.5 Hz, 2H, CH2-1'/CH-7), 2.40 (m, 2H, $CH_2$-2), 1.86 (m, 2H), 1.45 (m, 21H), 0.92 (t, J=6.6 Hz, 3H, $CH_3$-8') ppm. $^{13}$C NMR (MeOD-$d_4$, δ): 174.4 (CO), 170.2 (CO), 162.7 (C-7"), 137.0 (C-6"), 75.8 (CH-⅔"), 73.8 (CH-⅔"), 72.9 ($CH_2$-1'), 67.5 ($CH_2$-1"), 66.6 (CH-2"), 64.2 ($CH_2$), 35.9 (CH-4), 31.8 ($CH_2$), 31.6 ($CH_2$), 31.2 ($CH_2$), 31.1 ($CH_2$), 29.8 ($CH_2$), 29.2 ($CH_2$), 29.1 ($CH_2$), 28.9 ($CH_2$), 26.7 ($CH_2$), 26.1 ($CH_2$), 22.3 ($CH_2$), 13.6 ($CH_3$-8') ppm. MS (ESI) [m/z, (%)]: 533 (100), 443 ([$M^+$+1], 40), 411 (23), 144 (31). HR-MS (ESI): 443.2635 calculated for $C_{23}H_{38}O_8$ and found 443.2626.

Example 22. Preparation of 4-(((tert-butyldiphenyl-silyl)oxy)methyl)cyclohexan-1-ol (Compound 2)

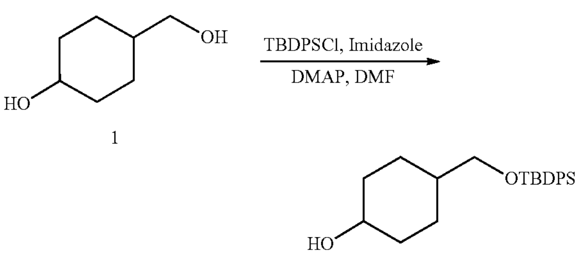

1

2

To a solution of diol 1 (5.0 g, 0.03 mol) in DMF (100 mL) were added Imidazole (10.5 g, 0.15 mol), a catalytic amount of DMAP and TBDPSCl (10.5 mL, 0.04 mol) and the mixture was stirred for 4 h. at room temperature. The solvent was evaporated, ethylacetate (20 mL) added and the product washed with $H_2O$ (3x20 mL). The organic layer was dried over $Na_2SO_4$, filtered and the solvent evaporated under reduced pressure. The residue was purified by column chromatography with ethylacetate-hexane (15%) to give compound 2 (13.9 g, 99%). Compound 2: Colourless oil, Rf: 0.60 (30% ethylacetate/hexane). IR (ATR, $cm^{-1}$): 3350, 2927, 2859, 1427, 1110, 701. MS (ESI) [m/z, (%)]: 369 ([$M^+$+1], 100), 351 ([$M^+$-OH], 21). HRMS (ESI): 369.2244 calculated for $C_{23}H_{33}O_2Si$ and found 369.2241.

Example 23. Preparation of 4-(((tert-butyldiphenyl-silyl)oxy)methyl)cyclohexan-1-one (Compound 3)

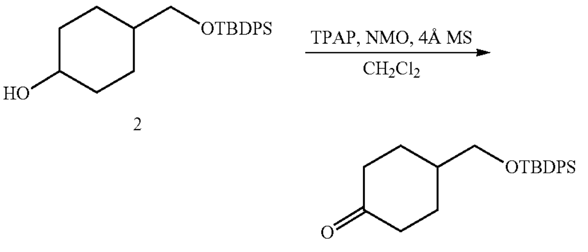

2

3

To a solution of compound 2 (1.4 g, 3.77 mmol) in $CH_2Cl_2$ (20 mL) were added molecular sieves (1.4 g), NMO (1.3 g, 11.30 mmol) and a catalytic amount of TPAP and stirring was continued at room temperature for 45 min. The reaction was filtered under celite and the solvent evaporated under reduced pressure. The residue was purified by column chromatography with ethylacetate-hexane (10%) to give compound 3 (1.0 g, 74%). Compound 3: Colourless oil, Rf:

0.70 (30% ethylacetate/hexane). IR (ATR, $cm^{-1}$): 2953, 2928, 2856, 1713. MS (ESI) [m/z, (%)]: 389 ([$M^+$+Na], 3), 289 ([$M^+$-Ph], 100). HRMS (ESI): 389.1907 calculated for $C_{23}H_{30}NaO_2Si$ and found 389.1906.

Example 24. Preparation of tert-butyl((4-hexylidenecyclohexyl)methoxy)diphenylsilane (Compound 4)

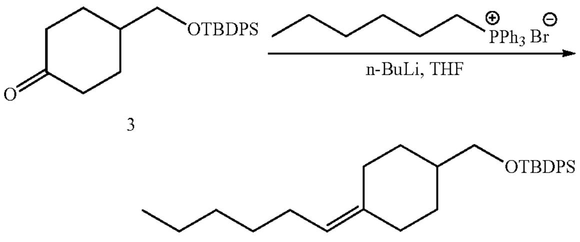

3
4

On the suspension of [$Ph_3PC_6H_{13}$]Br (6.0 g, 13.95 mmol) in THF (10 mL) cooled to 0° C. was added a 2.5 M solution of n-BuLi (5.1 mL, 12.70 mmol), the mixture was stirred for 1 h. Compound 3 (852 mg, 2.30 mmol) in THF (5 mL) was added and stirring was continued at room temperature for 48 h. The reaction was quenched with a saturated solution of $NaHCO_3$ (20 mL) and it was extracted with $^t$BuOMe (3×20 mL). The organic layer was dried over $Na_2SO_4$, filtered and the solvent evaporated under reduced pressure. The residue was purified by column chromatography with ethylacetate-hexane (1%) to give compound 4 (845 mg, 84%). Compound 4: Colourless oil, Rf: 0.82 (10% ethylacetate/hexane). IR (ATR, $cm^{-1}$): 2954, 2926, 2855. MS (ESI) [m/z, (%)]: 435 ([$M^+$+1], 40), 265 (100). HRMS (ESI): 435.3077 calculated for $C_{29}H_{43}OSi$ and found 435.3073.

Example 25. Preparation of (4-hexylidenecyclohexyl)metanol (Compound 5)

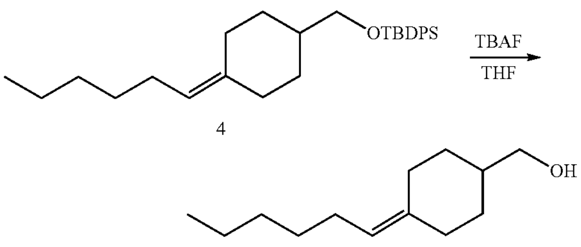

4
5

To a solution of compound 4 (2.4 g, 5.50 mmol) in THF (20 mL) was added a 1.0 M solution of TBAF (6.6 mL, 6.60 mmol) at room temperature and the mixture was stirred for 19 h in the same conditions. The solvent was evaporated and the residue was chromatographed on silica gel using ethylacetate-hexane (5%) as eluent affording compound 5 (1.0 g, 99%). Compound 5: Colourless oil, Rf: 0.30 (10% ethylacetate/hexane). IR (ATR, $cm^{-1}$): 3338, 2953, 2917, 2852. MS (ESI) [m/z, (%)]: 198 (15), 197 ([$M^+$+1], 100), 179 (19). HRMS (ESI): 197.1899 calculated for $C_{13}H_{25}O$ and found 197.1898.

Example 26. Preparation of ethyl (E)-3-(4-hexylidenecyclohexyl)acrylate (Compound 6)

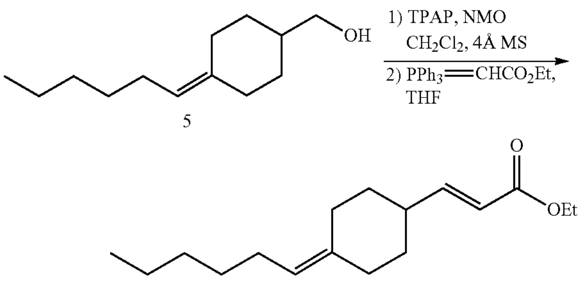

5
6

To a solution of compound 5 (213 mg, 1.17 mmol) in $CH_2Cl_2$ (4 mL) were added molecular sieves (200 mg), NMO (411 mg, 3.51 mmol) and a catalytic amount of TPAP and stirring was continued at room temperature for 1 h. The reaction was filtered under celite. The solvent was evaporated and the residue was dissolved in THF (5 mL) and $Ph_3P$=$CHCO_2Et$ (850 mg, 2.34 mmol) added, the mixture was stirred for 23 h. The solvent was evaporated and the residue was chromatographed on silica gel using ethylacetate-hexane (1%) as eluent affording compound 6 (204 mg, 66%). Compound 6: Colourless oil, Rf: 0.42 (5% ethylacetate/hexane). IR (ATR, $cm^{-1}$): 3404, 2955, 2923, 2870, 2854, 1718, 1650.

MS (ESI) [m/z, (%)]: 266 (18), 265 ([$M^+$+1], 100). HRMS (ESI): 265.2162 calculated for $C_{17}H_{29}O_2$ and found 265.2159.

Example 27. Preparation of ethyl 3-(4-hexylcyclohexyl)propanoate (Compound 7)

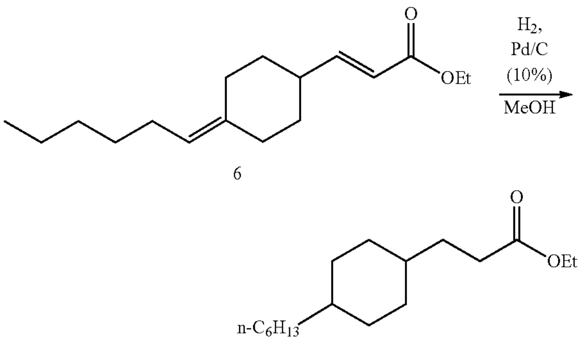

6
7

To a mixture of compound 6 (555 mg, 2.10 mmol) in MeOH (5 mL) was added a catalytic amount of Pd/C (10%) and the suspension was stirred for 24 h. at room temperature under $H_2$. The mixture was then filtered through celite and the filtrate was rotatory evaporated. The organic layer was dried over $Na_2SO_4$, filtered and the solvent evaporated under reduced pressure to give compound 7 (550 mg, 99%). Compound 7: Colourless oil, Rf: 0.70 (20% ethylacetate/hexane). IR (ATR, $cm^{-1}$): 2954, 2918, 2870, 2850, 1736.

MS (ESI) [m/z, (%)]: 270 (19%), 269 ([$M^{+}$+1], 100). HRMS (ESI): 269.2475 calculated for $C_{17}H_{33}O_2$ and found 269.2473.

Example 28. Preparation of 3-(4-hexylcyclohexyl)propanoic acid (Compound 8)

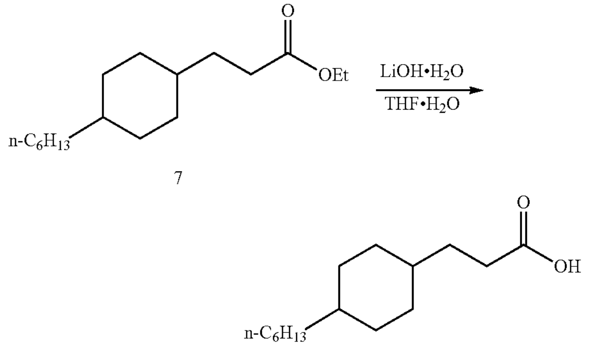

7

8

To a solution of compound 7 (169 mg, 0.63 mmol) in THF/$H_2O$ (1:1, 4 mL) and LiOH. $H_2O$ (79 mg, 1.89 mmol) added, the mixture was stirred at room temperature for 7 days. HCl 10% (2 mL) added and the product was extracted with $CH_2Cl_2$ (3x5 mL). The organic layer was dried over $Na_2SO_4$, filtered and the solvent evaporated under reduced pressure. The residue was purified by column chromatography with ethylacetate-hexane (10%) to give compound 8 (142 mg, 94%). Compound 8: Colourless oil, Rf: 0.40 (20% ethylacetate/hexane). IR (ATR, $cm^{-1}$): 3039, 2955, 2918, 2870, 2850, 1705. MS (ESI) [m/z, (%)]: 241 ([$M^{+}$+1], 100), 223 (44), 219 (63), 205 (65). HRMS (ESI): 241.2162 calculated for $C_{15}H_{29}O_2$ and found 241.2161.

Example 29. Preparation of(S)-2-((R)-3,4-bis(benzyloxy)-5-oxo-2,5-dihydrofuran-2-yl)-2-hydroxyethyl 3-(4-hexylcyclohexyl)propanoate (Compound 9)

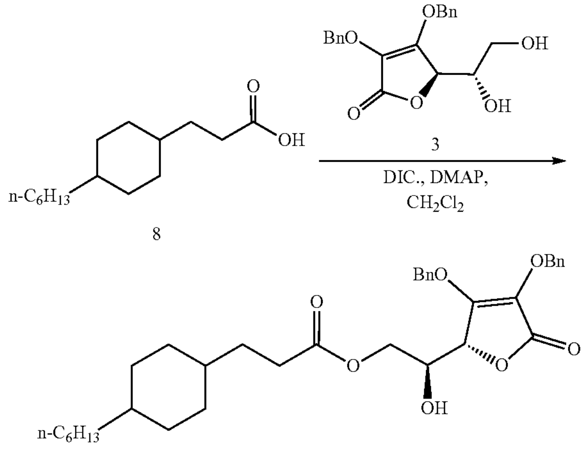

8

3

9

To a stirred solution of compound 8 (187 mg, 0.78 mmol) in $CH_2Cl_2$ (5 mL) was added DIC (132.0 μl, 0.86 mmol) and DMAP (79 mg, 0.78 mmol) and the mixture was stirred for 30 min. Protected vitamin C 3 (418 mg, 1.17 mmol) was added dropwise in $CH_2Cl_2$ (5 mL) and the reaction mixture was stirred overnight at room temperature and then filtrated. The filtrate was concentrated under reduced pressure. The residue was purified by column chromatography with ethylacetate-hexane (15%) to give compound 9 (290 mg, 64%). Compound 9: Colourless oil, Rf: 0.70 (20% ethylacetate/hexane). IR (ATR, $cm^{-1}$): 3404, 2953, 2919, 2850, 1761, 1742, 1671. MS (ESI) [m/z, (%)]: 579 ([$M^{+}$+1], 100), 367 (34), 269 (84). HRMS (ESI): 579.3316 calculated for $C_{35}H_{47}O_7$ and found 579.3303.

Example 30. Preparation of(S)-2-((R)-3,4-dihydroxy-5-oxo-2,5-dihydrofuran-2-yl)-2-hydroxyethyl 3-(4-hexylcyclohexyl)propanoate (Compound $I_b$)

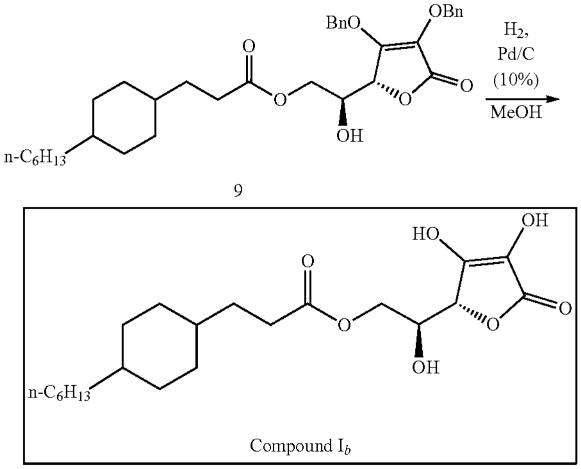

9

Compound $I_b$

To a mixture of compound 9 (44 mg, 0.07 mmol) in methanol (4 mL) was added a catalytic amount of Pd/C (10%) and the suspension was stirred for 4 h at room temperature under $H_2$. The mixture was then filtered through celite and the filtrate was rotatory evaporated, affording $I_b$ (23 mg, 74%). Compound $I_b$: Colourless oil, Rf: 0.09 (ethylacetate). IR (ATR, $cm^{-1}$): 3378, 2889, 2837, 1757. $^{1}H$-NMR (MeOD-$d_4$, δ): 4.78 (m, 8H), 4.22 (m, 3H, $CH_2$-1", CH-2"), 2.41 (m, 2H, $CH_2$-2), 1.78 (m, 4H), 1.55 (m, 4H), 1.19 (m, 14H), 0.92 (m, 3H, $CH_3$-6') ppm. $^{13}C$-NMR (MeOD-$d_4$, δ): 174.1 (CO), 171.8 (CO), 152.6 (C-7"), 118.7 (C-6"), 75.8 (CH-3"), 66.7 (CH-2"), 64.4 ($CH_2$-1"), 37.7 (CH-4/7), 37.3 (CH-4/7), 37.3 ($CH_2$-2), 32.9 ($CH_2$), 32.7 ($CH_2$), 32.0 ($CH_2$), 31.7 ($CH_2$), 31.2 ($CH_2$), 29.4 ($CH_2$), 28.5 ($CH_2$), 28.3 ($CH_2$), 26.7 ($CH_2$), 22.4 ($CH_2$), 13.1 ($CH_3$-6') ppm. MS (ESI) [m/z, (%)]: 416 (100), 399 ([$M^{+}$+1], 49), 367 (72), 282 (29). HRMS (ESI): 399.2377 calculated for $C_{21}H_{35}O_7$ and found 399.2372.

Example 31: Cell Culture and Treatment of Cells with the Compounds of the Invention Cell Cultures The BXPC3, CAPAN2, RWP1 cell lines from human pancreatic cancer were provided by the Biomedical Research Institute (IRB) Barcelona; the MW115 and IGR39 cell lines from human primary melanoma and MW 266.4 and IGR37 from human metastatic melanoma were provided by Dr. Manel Esteller from the Catalan Institute of Oncology (ICO) Barcelona (Vizoso M. et al., "Epigenetic activation of a cryptic TBC1D16 transcript enhances melanoma progression by targeting EGFR" Nat Med., 2015, vol 21 (7), pp. 741-50); DLDL1, SW480 and HCT116 cell lines from human colon cancer were provided by Dra. Neus Agell from the Research Institute August Pi Sunyer (IDIBAPS)-University of Barcelona (UB); NUG-C4 and COLO668 cell lines from human gastric and lung cancers, respectively, were provided by the Center for Genomic Regulation (CRG) Barcelona. Human primary endothelial cells from umbilical cord (HUVEC) and from aorta (HAEC) were obtained directly by the investigator Dra. Teresa Royo and stored in liquid nitrogen in the laboratory. BXPC3, CAPAN2 and DLD1 cell lines were maintained in RPMI-1640 culture medium, SW480 and HCT116 in DMEM/HAM, RWP1 and all the melanoma cell lines were maintained in DMEM and cell culture mediums (Gibco) were all supplemented with 10% fetal bovine serum and antibiotics. HUVEC and HAEC primary cells were maintained in M199 culture medium (Gibco) supplemented with 20% fetal bovine serum, endothelial cell growth supplement (ECGS), Heparin (Hep) and antibiotics. Cultures were maintained in the cell incubator in a humid atmosphere at 37° C. containing 5% $CO_2$.

The different compounds to be tested were easily dissolved in 100% methanol at a concentration of 0.5 M and subsequently a 0.1 M intermediate dilution was prepared in 100% ethanol. From this latter dilution, the different treatments at the established concentrations were prepared in the corresponding supplemented medium. The different treatments were prepared at a double concentration and 100 µl of them were added to the same volume of cell growth medium in the wells to reach the final concentrations (from 0.1 to 0.3 mM-0.1, 0.2, 0.25 and 0.3 mM).

Cell Treatments

Assays with the different compounds were performed in 96 well plates following the protocol explained below.

The cells were resuspended by trypsin/EDTA digestion with 0.5% Trypsin-EDTA in the case of different human cancer cell lines, and 0.25% Trypsin-EDTA in the case of human primary endothelial cells. Once resuspended in culture medium, they were counted in Newbauer chamber after a 1:1 dilution with trypan blue. This staining allows the number of living cells in the suspension to be known. From the counting, a suitable dilution of the cells (5000 or 10000 cells/100 µl/well in 96 well plates depending on the growth rate of the different cell types) was prepared. Cells were left 48 hours in culture within the cell incubator. After 48 hours of incubation, 100 µl/well of a double concentrated solution of the compounds prepared as explained above were added. Treatments were then maintained for 72 hours by keeping the cells in the cell incubator.

After 72 hours, the culture media was removed by decantation, cells were washed twice with DPBS and then cells were fixed with 100 µl of 4% paraformaldehyde solution for 30 min. Two washes were then performed with 100 µl of mQ $H_2O$ and immediately 50 µl of 0.25% Violet Crystal solution, prepared in distilled water, were added and maintained for 30 min at RT. At the end of the staining time, several washes with distilled water were performed to completely remove the excess of Violet Crystal, the plates were then completely dried in the oven at 37° C.

The optical density values per well were obtained by a Biotek Synergy™2 multi-detection microplate reader, using a 590 nm filter and by scanning reading, obtaining the mean values per well.

Results

As can be observed in FIGS. 1-12 when primary or metastatic human cancer cells from various origins were treated with compounds of the invention at increasing concentrations the growth of cancer cells was significantly reduced.

Moreover, the compound $I_b$ showed a remarkable inhibitory capacity even at concentrations as low as 0.2 mM.

Figure 13:
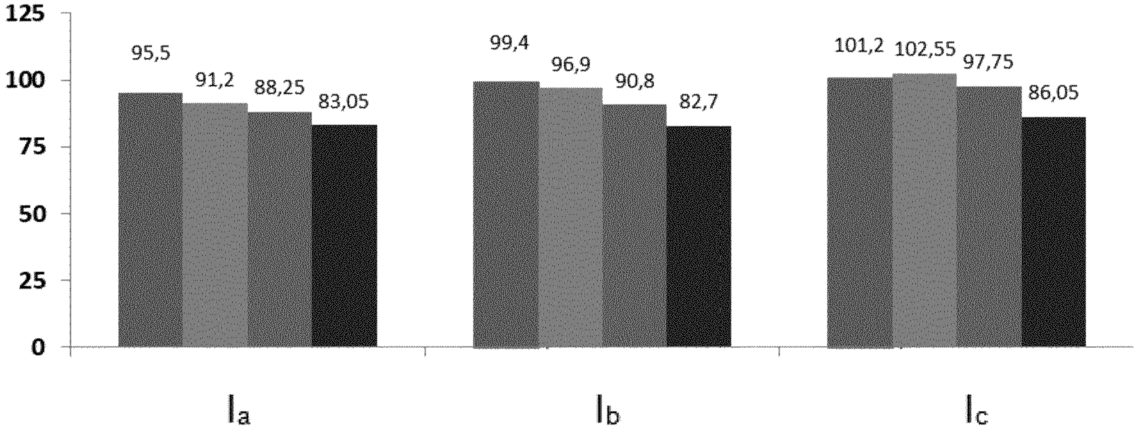
FIG. 13, is a bar diagram showing the inhibitory effect of various compounds of the invention on the growth of human primary vascular endothelial cells in comparison to mock treated cells. The above description of FIG. 1 regarding the columns, compounds, and y-axis equally apply to this Figure.

Notably, the administration of the compounds of the invention did not significantly affect the growth of normal non-transformed cells. This lack of significant toxicity was maintained independently of the dose of the peptide applied (ranging from 0.1 mM up to 0.3 mM FIG. 13).

These results unambiguously demonstrate the high therapeutic potential of the compounds of the invention as anti-cancer agents given their low toxicity in non-transformed cells and their high growth-inhibitory activity in cancer cells, both primary and metastatic.

CITATION LISTS

T. W. Greene and P. G. M. Wuts, "Protective Groups in Organic Synthesis", Chapter 2, Protection for the Hydroxyl Group, Including 1,2- and 1,3-Diols, John Wiley & Sons, Inc., 1999, pp. 17-245.

Vizoso M. et al "Epigenetic activation of a cryptic TBC1D16 transcript enhances melanoma progression by targeting EGFR" Nat Med., 2015, vol 21(7), pp. 741-50

The invention claimed is:

1. A compound of formula (I), or a pharmaceutically acceptable salt thereof, or a stereoisomer thereof or mixture of stereoisomers, (I)

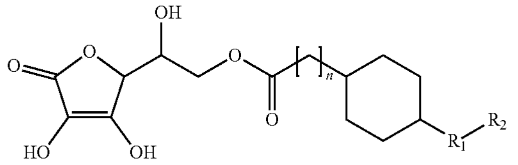

wherein:

n is an integer from 0 to 10;

$R_1$ is a biradical selected from the group consisting of $CH_2$, O, NH and S; and $R_2$ is a $(C_3\text{-}C_{15})$alkyl radical.

2. The compound according to claim 1, wherein n is from 1 to 5.

3. The compound according to claim 1, wherein n is 2.

4. The compound according to claim 1, wherein $R_1$ is $CH_2$ or O.

5. The compound according to claim 1, wherein $R_2$ is $(C_4\text{-}C_9)$alkyl.

6. The compound according to claim 1, wherein $R_2$ is $(C_5)$alkyl.

7. The compound according to claim 1, wherein:

n is 2;

$R_1$ is $CH_2$; and $R_2$ is $(C_5)$alkyl.

8. A pharmaceutical composition comprising a therapeutically effective amount of the compound as defined in claim 1, with at least one pharmaceutically acceptable excipient, diluent, or carrier.

9. A method for treating or preventing a neoplastic disease, wherein the neoplastic disease is selected from the group consisting of pancreatic cancer, melanoma, colon cancer, gastric cancer, and lung cancer, the method comprising administering to a subject in need thereof a therapeutically effective amount of the compound as defined in claim 1 together with one or more pharmaceutically acceptable excipient or carrier.

10. The method according to claim 9, wherein the neoplastic disease is pancreatic cancer.

11. A preparation process of a compound of formula (I) as defined in claim 1, comprising:

a) submitting a compound of formula (II) to a esterification reaction with a compound of formula (III), and b) deprotecting the resulting compound from (a);

wherein:

n is an integer from 0 to 10;

$R_1$ is a biradical selected from the group consisting of $CH_2$, O, NH and S;

$R_2$ is a $(C_3\text{-}C_{15})$alkyl radical; and

PG is a hydroxyl protective group.

(II)

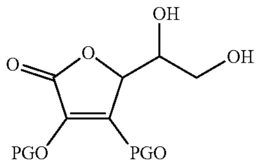

(III)

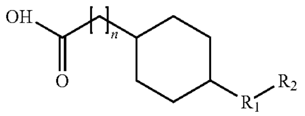

12. The preparation process according to claim 11, wherein:

n is 2;

$R_1$ is $CH_2$; and $R_2$ is $(C_5)$alkyl.

* * * * *